United States Patent
Myhren et al.

(10) Patent No.: US 11,819,509 B2
(45) Date of Patent: *Nov. 21, 2023

(54) LIPID COMPOSITIONS

(71) Applicant: Aker BioMarine Antarctic AS, Stamsund (NO)

(72) Inventors: Finn Myhren, Oslo (NO); Nils Hoem, Oslo (NO); Asgeir Saebo, Eidsnes (NO); Anil R. Oroskar, Oak Brook, IL (US); Asha A. Oroskar, Oak Brook, IL (US); Anantha Krishna Mallia, Rockford, IL (US)

(73) Assignee: Aker BioMarine Antarctic AS, Stamsund (NO)

(*) Notice: Subject to any disclaimer, the term of this patent is extended or adjusted under 35 U.S.C. 154(b) by 335 days.

This patent is subject to a terminal disclaimer.

(21) Appl. No.: 17/116,418

(22) Filed: Dec. 9, 2020

(65) Prior Publication Data

US 2021/0085698 A1     Mar. 25, 2021

Related U.S. Application Data

(63) Continuation of application No. 15/040,347, filed on Feb. 10, 2016, now Pat. No. 10,864,223.

(60) Provisional application No. 62/114,811, filed on Feb. 11, 2015.

(51) Int. Cl.
| | |
|---|---|
| *A61K 31/215* | (2006.01) |
| *A61K 31/20* | (2006.01) |
| *A61K 9/00* | (2006.01) |
| *A23K 20/179* | (2016.01) |
| *A23K 20/158* | (2016.01) |
| *A23K 20/26* | (2016.01) |
| *A23L 33/12* | (2016.01) |
| *A61K 31/685* | (2006.01) |
| *A61K 31/23* | (2006.01) |
| *A61K 31/683* | (2006.01) |
| *A61K 35/612* | (2015.01) |
| *C11B 3/16* | (2006.01) |
| *C11B 3/00* | (2006.01) |

(52) U.S. Cl.
CPC .......... *A61K 31/685* (2013.01); *A23K 20/158* (2016.05); *A23K 20/179* (2016.05); *A23K 20/26* (2016.05); *A23L 33/12* (2016.08); *A61K 9/0053* (2013.01); *A61K 31/20* (2013.01); *A61K 31/215* (2013.01); *A61K 31/23* (2013.01); *A61K 31/683* (2013.01); *A61K 35/612* (2013.01); *C11B 3/006* (2013.01); *C11B 3/16* (2013.01)

(58) Field of Classification Search
CPC ..... A23L 33/12; A23K 20/158; A61K 31/685; A61K 31/23; A61K 31/215; A61K 35/612
See application file for complete search history.

(56) References Cited

U.S. PATENT DOCUMENTS

| | | |
|---|---|---|
| 2,652,235 A | 9/1953 | Samuelsen |
| 4,036,993 A | 7/1977 | Ikeda |
| 4,038,722 A | 8/1977 | Terase et al. |
| 4,119,619 A | 10/1978 | Rogozhin et al. |
| 4,133,077 A | 1/1979 | Jasniewicz |
| 4,251,557 A | 2/1981 | Shimose et al. |
| 4,505,936 A | 3/1985 | Meyers et al. |
| 4,714,571 A | 12/1987 | Kearns et al. |
| 4,749,522 A | 6/1988 | Kamarei |
| 4,814,111 A | 3/1989 | Kearns et al. |
| 5,006,281 A | 4/1991 | Rubin et al. |
| 5,266,564 A | 11/1993 | Modolell |
| 5,434,183 A | 7/1995 | Larsson-Backstrom |
| 6,214,396 B1 | 4/2001 | Barrier |
| 6,346,276 B1 | 2/2002 | Tanouchi et al. |
| 6,537,787 B1 | 3/2003 | Breton |
| 6,800,299 B1 | 10/2004 | Beaudoin |
| 7,488,503 B1 | 2/2009 | Porzio et al. |
| 7,666,447 B2 | 2/2010 | Rockway |
| 8,030,348 B2 | 10/2011 | Sampalis |
| 8,057,825 B2 | 11/2011 | Sampalis |
| 8,278,351 B2 | 10/2012 | Sampalis |
| 8,372,812 B2 | 2/2013 | Tilseth et al. |
| 8,383,675 B2 | 2/2013 | Sampalis |
| 8,697,138 B2 | 4/2014 | Bruheim et al. |
| 9,028,877 B2 | 5/2015 | Bruheim et al. |
| 9,034,388 B2 | 5/2015 | Bruheim et al. |
| 9,072,752 B1 | 7/2015 | Bruheim et al. |
| 9,078,905 B2 | 7/2015 | Bruheim et al. |
| 9,119,864 B2 | 9/2015 | Bruheim et al. |
| 10,864,223 B2 * | 12/2020 | Myhren .................. A61K 31/23 |
| 2002/0076468 A1 | 6/2002 | Saxby |

(Continued)

FOREIGN PATENT DOCUMENTS

| | | |
|---|---|---|
| AU | 2002322233 | 2/2003 |
| BR | 8701265 | 3/1987 |

(Continued)

OTHER PUBLICATIONS

Declaration of Bjorn Ole Haugsgjerd submitted during inter partes reexamination of parent U.S. Pat. No. 8,030,348 ("Haugsgjerd '348 Decl.").

(Continued)

*Primary Examiner* — Theodore R. Howell

(74) *Attorney, Agent, or Firm* — CASIMIR JONES S.C.; J. Mitchell Jones

(57) ABSTRACT

The present invention provides improved processes for extracting and preparing lipids from biological sources for use in pharmaceuticals, nutraceuticals and functional foods.

16 Claims, No Drawings

(56) References Cited

U.S. PATENT DOCUMENTS

| | | |
|---|---|---|
| 2003/0044495 A1 | 3/2003 | Kagan |
| 2003/0113432 A1 | 6/2003 | Yoshitomi |
| 2004/0241249 A1 | 12/2004 | Sampalis |
| 2005/0003073 A1 | 1/2005 | Pivovarov et al. |
| 2006/0078625 A1 | 4/2006 | Rockway |
| 2006/0193962 A1 | 8/2006 | Kamiya et al. |
| 2008/0166419 A1 | 7/2008 | Sones |
| 2008/0166420 A1 | 7/2008 | Sones |
| 2008/0274203 A1* | 11/2008 | Bruheim ............ A61K 31/215 514/121 |
| 2009/0061067 A1 | 3/2009 | Tilseth et al. |
| 2010/0143571 A1 | 6/2010 | Breivik |
| 2010/0160659 A1 | 6/2010 | Catchpole |
| 2010/0226977 A1 | 9/2010 | Tilseth et al. |
| 2011/0130458 A1 | 6/2011 | Breivik |
| 2014/0005421 A1 | 1/2014 | Bruheim et al. |
| 2014/0010888 A1 | 1/2014 | Bruheim et al. |
| 2014/0080791 A1 | 3/2014 | Berge et al. |
| 2014/0088043 A1 | 3/2014 | Hoem et al. |
| 2014/0088047 A1 | 3/2014 | Hoem et al. |
| 2014/0107072 A1 | 4/2014 | Tilseth et al. |
| 2014/0274968 A1 | 9/2014 | Berge et al. |
| 2014/0363517 A1 | 12/2014 | Bruheim et al. |
| 2014/0370115 A1 | 12/2014 | Hoem et al. |
| 2015/0030718 A1 | 1/2015 | Saebo |
| 2015/0050403 A1 | 2/2015 | Tilseth et al. |
| 2015/0164841 A1 | 6/2015 | Hoem et al. |

FOREIGN PATENT DOCUMENTS

| | | |
|---|---|---|
| CA | 1098900 | 4/1981 |
| CA | 2251265 | 4/2000 |
| CL | 40348 | 7/1997 |
| CN | 102746941 | 1/2014 |
| EP | 0609078 | 8/1994 |
| EP | 0670306 | 6/1995 |
| EP | 1127497 | 8/2001 |
| EP | 1392623 | 3/2004 |
| EP | 1406641 | 4/2004 |
| EP | 1631280 | 4/2004 |
| EP | 1542670 | 6/2005 |
| EP | 0973532 | 9/2005 |
| EP | 1689413 | 8/2006 |
| EP | 1660071 | 1/2007 |
| EP | 1743531 | 1/2007 |
| EP | 1123368 | 4/2008 |
| EP | 1419768 | 1/2009 |
| EP | 1292294 | 3/2009 |
| EP | 1706106 | 7/2009 |
| EP | 1385500 | 7/2010 |
| GB | 2097014 | 10/1982 |
| GB | 921537 | 6/1999 |
| JP | S51-125774 | 11/1976 |
| JP | S52-114046 | 9/1977 |
| JP | 60-153779 | 8/1985 |
| JP | 61281159 | 12/1986 |
| JP | 02049091 | 2/1990 |
| JP | 2215351 | 8/1990 |
| JP | 4012665 | 1/1992 |
| JP | 2963152 | 2/1992 |
| JP | 04057853 | 2/1992 |
| JP | 3081692 | 7/1994 |
| JP | 2524217 | 8/1996 |
| JP | H08-231391 | 8/1996 |
| JP | 3344887 | 7/1997 |
| JP | 3611222 | 8/1997 |
| JP | 2909508 | 6/1999 |
| JP | 2001-158736 | 6/2001 |
| JP | 2003-003192 | 1/2003 |
| JP | 2003-048831 | 2/2003 |
| JP | 2003-146883 | 5/2003 |
| JP | 3467794 | 9/2003 |
| JP | 2003-530448 | 10/2003 |
| JP | 3486778 | 10/2003 |
| JP | 2004-534800 | 11/2004 |
| JP | 3678317 | 5/2005 |
| JP | 2005-245379 | 9/2005 |
| JP | 2006-069948 | 3/2006 |
| JP | 2006-083136 | 3/2006 |
| JP | 2006-290784 | 10/2006 |
| JP | 2006-316073 | 11/2006 |
| JP | 2006-328014 | 12/2006 |
| JP | 2007-126455 | 5/2007 |
| JP | 2007-246404 | 9/2007 |
| SU | 220741 | 1/1971 |
| WO | 82/02819 | 9/1982 |
| WO | 1989/06082 | 10/1986 |
| WO | 89/01031 | 2/1989 |
| WO | 89/10960 | 11/1989 |
| WO | 1990/05765 | 5/1990 |
| WO | 1993/24142 | 12/1993 |
| WO | 97/38585 | 10/1997 |
| WO | 1997/38585 | 10/1997 |
| WO | 1997/39759 | 10/1997 |
| WO | 98/34498 | 8/1998 |
| WO | 1998/34498 | 8/1998 |
| WO | 99/39589 | 8/1999 |
| WO | 1999/39589 | 8/1999 |
| WO | 2000/23546 | 4/2000 |
| WO | 2000/25608 | 5/2000 |
| WO | 2000/38708 | 7/2000 |
| WO | 2001/028526 | 4/2001 |
| WO | 2001/082928 | 11/2001 |
| WO | 2002-083122 | 10/2002 |
| WO | 2002/083122 | 10/2002 |
| WO | 2002/092540 | 11/2002 |
| WO | 02/102394 | 12/2002 |
| WO | 2002/102394 | 12/2002 |
| WO | 2003/011873 | 2/2003 |
| WO | 2003/013497 | 2/2003 |
| WO | 2004/028529 | 4/2004 |
| WO | 2004/047554 | 6/2004 |
| WO | 2004/112767 | 12/2004 |
| WO | 05/004593 | 1/2005 |
| WO | 2005-018632 | 3/2005 |
| WO | 2005/037848 | 4/2005 |
| WO | 2005/038037 | 4/2005 |
| WO | 2005/070411 | 8/2005 |
| WO | 2006/030552 | 3/2006 |
| WO | 2004-100943 | 5/2006 |
| WO | 06/111633 | 10/2006 |
| WO | 07/080515 | 7/2007 |
| WO | 2007/080514 | 7/2007 |
| WO | 2007/080515 | 7/2007 |
| WO | 2007/108702 | 9/2007 |
| WO | 07/123424 | 11/2007 |
| WO | 2008/006607 | 1/2008 |
| WO | 08/072563 | 6/2008 |
| WO | 08/117062 | 10/2008 |
| WO | 2008/117062 | 10/2008 |
| WO | 2009/027692 | 3/2009 |
| WO | 2010/097701 | 9/2010 |
| WO | 2013/102792 | 7/2013 |
| WO | 2014/013335 | 1/2014 |

OTHER PUBLICATIONS

Declaration of Dr. Albert Lee in Support of Inter Partes Review of U.S. Pat. No. 8,278,351 ("Lee").

Declaration of Dr. Albert Lee in Support of Inter Partes Review of U.S. Pat. No. 8,383,675 ("Lee").

Declaration of Dr. Chong Lee submitted during inter partes reexamination of parent U.S. Pat. No. 8,030,348 ("Yeboah Reexam Decl.").

Declaration of Dr. Earl White submitted during prosecution of parent U.S. Pat. No. 8,030,348 ("2011 White Decl.").

Declaration of Dr. Ivar Storm in support of Inter Partes Review of U.S. Pat. No. 8,278,351 ("Storms").

Declaration of Dr. Ivar Storm in support of Inter Partes Review of U.S. Pat. No. 8,383,675 ("Storms").

Declaration of Dr. Jacek Jaczynski from inter partes reexamination of the parent U.S. Pat. No. 8,030,348 ("Jaczynski Reexam. Decl.").

(56) References Cited

OTHER PUBLICATIONS

Declaration of Dr. Jaczynski submitted during prosecution of parent U.S. Pat. No. 8,278,351 (Jaczynski '351 Decl.).
Declaration of Dr. Jeff Moore in Support of Inter Partes Review of U.S. Pat. No. 8,278,351 ("Moore").
Declaration of Dr. Jeff Moore in Support of Inter Partes Review of U.S. Pat. No. 8,383,675 ("Moore").
Declaration of Dr. Richard van Breemen in Support of Inter Partes Review of U.S. Pat. No. 8,278,351 ("Van Breemen").
Declaration of Dr. Richard van Breemen in Support of Inter Partes Review of U.S. Pat. No. 8,383,675 ("Van Breemen").
Declaration of Dr. Shahidi submitted during inter partes reexamination of parent U.S. Pat. No. 8,030,348 (Shahidi Reexam. Decl.).
Declaration of Dr. Shahidi submitted during prosecution of parent U.S. Pat. No. 8,278,351 (Shahidi '351 Decl.).
Declaration of Dr. Suzanne Budge in Support of Inter Partes Review of U.S. Pat. No. 8,278,351 ("Budge").
Declaration of Dr. Suzanne Budge in Support of Inter Partes Review of U.S. Pat. No. 8,383,675 ("Budge").
Declaration of Dr. Thomas Brenna in support of Inter Partes Review of U.S. Pat. No. 8,278,351.
Declaration of Dr. Thomas Brenna in support of Inter Partes Review of U.S. Pat. No. 8,383,675.
Declaration of Dr. Thomas Gundersen submitted during inter partes reexamination of parent U.S. Pat. No. 8,030,348 ("Gundersen Decl.").
Declaration of Dr. Tina Sampalis submitted during inter partes reexamination of parent U.S. Pat. No. 8,030,348 (Sampalis).
Declaration of Dr. Van Breemen submitted during Ex parte Reexamination of the '351 patent (Van Breemen '351 Reexam. Decl.
Declaration of Dr. Van Breemen submitted during Inter partes Reexamination of the '348 patent (Van Breemen '348 Reexam Decl.
Declaration of Dr. Yeboah submitted during inter partes reexamination of parent U.S. Pat. No. 8,030,348 ("Yeboah Reexam Decl.").
Declaration of Dr. Yeboah submitted during prosecution of parent U.S. Pat. No. 8,278,351 ("Yeboah '351 Decl.").
Eichberg, "Lecithin—It Manufacture and Use in the Fat and Oil Industry," Oils and Soap 51-54, 1939 ("Eichberg").
Expert Witness Report of Dr. Theodore Welch submitted in relation to ITC Investigation No. 337-TA-877 ("Welch").
Farkas, Composition and Physical State of Phospholipids in Calanoid Copepods from India and Norway, Lipids, vol. 23, No. 6 (1988).
Final Prospectus dated May 11, 2001 ("Final Prospectus").
Folch, et al., A Simple Method for the Isolation and Purification of Total Lipids from Animal Tissues. J. Biol. Chem., 226, 497-509 (1957).
Grant of Request for Ex parte Reexamination of the '351 patent.
Grit et al., Hydrolysis of phosphatidylcholine in aqueous liposome dispersions, Int. J. Pharmaceutics 50:1-6 (1989).
Henderson et al., Lipid Composition of the Pineal Organ from Rainbow Trout (*Oncorhynchus mykiss*), Lipids, vol. 29, No. 5, pp. 311-317 (1994) ("Henderson ").
Herman and Groves, The Influence of Free Fatty Acid Formation on the pH of Phospholipid-Stabilized Triglyceride Emulsions, Pharmaceutical Research 10(5):774-776 (1993).
Itano Refrigerated Food Co., Ltd., Bio & High Technology Announcement and Natural Astaxanthin & Krill Lecithin, pp. 1-16 (on or before Dec. 28, 1994) ("Itano").
Johnson and Lucas, Comparison of Alternative Solvents for Oils Extraction, JAOCS 60(2):229-242 (1983).
Le Grandois et al., Investigation of Natural Phosphatidylcholine Sources: Separation and Identification by Liquid Chromatography—Electrospray Ionization—Tandem Mass Spectrometry (LC-ESI-MS2) of Molecular Species, J. Agric. Food Chem., 57, 6014-20 (2009) ("Le Grandois").
Lin et al., Effect of Dietary N-3 Fatty Acids Upon the PhospholipidMolecular Species of the Monkey Retina, Invest Ophthalmol Vis Sci. 1994;35:794-803.
Medina et al., C Nuclear Magnetic Resonance Monitoring of Free Fatty Acid Release After Fish Thermal Processing, J. Amer. Oil Chem. Soc. 71(5):479-82 (1994).
Oct. 24, 2012 Office Action, '675 patent.
Office Action dated Jan. 5, 2012, '351 patent.
U.S. Appl. No. 60/307,842 (Priority document for the '351 patent).
Supplemental Declaration of Bjorn Ole Haugsgjerd submitted during inter partes reexamination of parent U.S. Pat. No. 8,030,348 ("Haugsgjerd '348 Supp. Decl.").
Supplemental Declaration of Dr. Earl White submitted during inter partes reexamination of parent U.S. Pat. No. 8,030,348 ("White Supp. Reexam. Decl.").
Supplemental Declaration of Dr. Earl White submitted during prosecution of parent U.S. Pat. No. 8,278,351 ("White Supp. Decl.").
Supplemental Declaration of Dr. Thomas Gundersen submitted during inter partes reexamination of parent U.S. Pat. No. 8,030,348 ("Gundersen Supp. Decl.").
Suzuki, T. and Shibata, N., "The utilization of Antarctic krill for human food," Food Rev. Int'l, 6:1, 119-147 (1990) ("Suzuki").
Takahashi et al., Compositional Changes in Molecular Species of Fish Muscle Phosphatidylcholine During Storage, Bull. Fac. Fish. Hokkaido Univ. 37(1), 80-84 1986.
Takahashi et al., Molecular Species of Fish Muscle Lecithin, Bulletin of the Japanese Society of Scientific Fisheries 48(12), 1803-1814 (1982).
Ando and Hatano, 1988, "Isolation of apolipoproteins from carotenoid-carrying lipoprotein in the serum of chum salmon, *Oncorhynchus keta*", J. Lipid Research, 29: 1264-1271.
Aoi et al., 2003, "Astaxanthin limits exercise-induced skeletal and cardiac muscle damage in mice", Antioxidants & Redox Signaling, 5(1): 139-44.
Britton, 1985, "General Carotenoid Methods", Methods in Enzymology, vol. 111, pp. 113-149.
Calder, 2006, "n-3 polyunsaturated fatty acids, inflammation, and inflammatory diseases", Am. J. Clin. Nutr., 83: 1505S.
Charest et al., 2001, "Astaxanthin Extraction from Crawfish Shells by Supercritical $CO_2$ with Ethanol as Cosolvent", J. Aquatic Food Product Technology, 10(3): 79-93.
Chen and Meyers, 1982, "Extraction of Astaxanthin Pigment from Crawfish Waste Using a Soy Oil Process", J. Food Sci., 47: 892-896.
Clarke, 1980, "The Biochemical Composition of Krill, *Euphausia superba* dana,from South Georgia", J. Exp. Mar. Biol. Ecol., 43: 221-236.
Czeczuga, 1974, "Comparative Studies of Carotenoids in the Fauna of the Gullmar Fjord (Bohuslan, Sweden). II. Crustacea: Eupagurus bernhardus, Hyas coarctatus and Upogebia deltaura", Marine Biology, 28: 95-98.
De Ritter and Purcell, 1981, "Carotenoid Analytical Methods", Carotenoids as Colorants and Vitamin A Precursors: Technological and Nutritional Applications, pp. 815-882.
Deutch, 1995, "Menstrual pain in Danish women correlated with low n-3 polyunsaturated fatty acid intake", Eur. J. Clin. Nutr., 49(7): 508-16.
Diez et al., 2003, "The role of the novel adipocyte-derived hormone adiponectin in human disease", Eur. J. Endocrinol., 148(3): 293-300.
Ellingsen et al., 1987, "Biochemistry of the autolytic processes in Antarctic krill post mortem. Autoproteolysis." Biochem. J. 246, 295-305.
Emodi, 1978, "Carotenoids: Properties and Applications", Food Technology, 32(5): 38.
Felix-Valenzuela et al., 2001, "Supercritical CO2/Ethanol Extraction of Astaxanthin from Blue Crab (*Callinectes sapidus*) Shell Waste", Journal of Food Process Engineering, 24: 101-112.
Fox and Scheer, 1941, "Comparative Studies of the Pigments of Some Pacific Coast Echinoderms", The Biological Bulletin, 441-455.
Geusens et al., 1994, "Long-term effect of omega-3 fatty acid supplementation in active rheumatoid arthritis. A 12-month, double-blind, controlled study", Arthritis Rheum., 37(6): 824-9.

(56) References Cited

OTHER PUBLICATIONS

Gilchrist and Green, 1960, "The Pigments of Artemia", Proceedings of the Royal Society, Series B Biological Sciences, vol. 152 No. 946, pp. 118-136.
Goodwin and Srisukh, 1949, "Some Observations on Astaxanthin Distribution in Marine Crustacea", Department of Biochemistry, University of Liverpool, pp. 268-270.
Gulyaev and Bugrova, 1976 Removing fats from the protein paste "Okean". Konservnaya I Ovoshchesushil'naya Promyshlennost, (4), 37-8.
Hardardottir and Kinsella, 1988, "Extraction of Lipid and Cholesterol from Fish Muscle with Supercritical Fluids" Journal of Food Science, 53(6): 1656-1658.
International Aqua Feed, 2006, vol. 9.
International Search Report and Written Opinion for PCT/GB2008/002934, dated Mar. 11, 2009.
International Search Report and Written Opinion for PCT/IB2010/000512; dated Jun. 24, 2010.
International Search Report for PCT/IB2007/000098, dated Jun. 26, 2007.
Itoh et al., 2007; "Increased adiponectin secretion by highly purified eicosapentaenoic acid in rodent models of obesity and human obese subjects", Arteriosclerosis, Thrombosis, and Vascular Biology; 27(9): 1918-1925.
Johnson et al., 1978, "Simple Method for the Isolation of Astaxanthin from the Basidiomycetous Yeast *Phaffia rhodozyma*", Applied and Environmental Microbiology, 35(6): 1155-1159.
Kolakowska, 1989, "Krill lipids after frozen storage of about one year in relation to storage time before freezing", Die Nahrung Food, 33(3): 241-244.
Kris-Etherton et al., 2002, "Fish Consumption, Fish Oil, Omega-3 Fatty Acids, and Cardiovascular Disease", Circulation, 106:2747-2757.
Kristensen et al., 1989, "Dietary supplementation with n-3 polyunsaturated fatty acids and human platelet function: a review with particular emphasis on implications for cardiovascular disease", J. Intern. Med. Suppl. 731:141-50.
Kunesova et al., 2006, "The influence of n-3 polyunsaturated fatty acids and very low calorie diet during a short-term weight reducing regimen on weight loss and serum fatty acid composition in severely obese women", Physiol Res.; 55(1):63-72.
Laight et al., 1999, "F2-isoprostane evidence of oxidant stress in the insulin resistant, obese Zucker rat: effects of vitamin E", Eur. J. Pharmacol. 377(1): 89-92.
Ambertson and Braekkan, 1971, "Method of Analysis of Astaxanthin and its Occurrence in some Marine Products," J. Sci. Food. Agr., vol. 22(2): 99-101.
Libby et al., 2006, "Inflammation and Atherothrombosis: From Population Biology and Bench Research to Clinical Practice", J. Amer. Coll. Card., 48 (9, Suppl. A): A33-A46.
Lopez et al., 2004, "Selective extraction of astaxanthin from crustaceans by use of supercritical carbon dioxide", Talanta, 64: 726-731.
Mandeville, 1991, "Isolation and Identification of Carotenoid Pigments, Lipids and Flavor Active Components from Raw Commercial Shrimp Waste", Food Biotechnology, 5(2): 185-195.
Meyers and Bligh, 1981, "Characterization of Astaxanthin Pigments from Heat-Processed Crawfish Waste", J. Agric. Food Chem., 29: 505-508.
Meyers, 1977, "Using Crustacean Meals and Carotenoid-Fortified Diets", Feedstuffs, vol. 49(19).
Meyers, 1994, "Developments in world aquaculture, feed formulations, and role of carotenoids", Pure & Appl. Chem, vol. 66(5): 1069-1076.
Mills et al., 1989, "Dietary N-6 and N-3 fatty acids and salt-induced hypertension in the borderline hypertensive rat", Lipids, 24(1): 17-24.
Moates and Van Bentem, 1990, "Separating out the value", Food Science and Technology Today, 4(4): 213-214.
Nikolaeva, 1967 "Amino acid composition of protein-coagulate in krill", VNIRO, 63:161-4.
Phleger, et al. (2002) "Interannual and between species comparison in the lipids, fatty acids, and sterols of Antarctic krill from the US AMLR Elephant Island survey area: 1997 and 1998". Comp Biochem Physiol 131B:733-747.
Popp-Snijders et al., 1987, "Dietary supplementation of omega-3 polyunsaturated fatty acids improves insulin sensitivity in non-insulin-dependent diabetes", Diabetes Res. 4(3): 141-7.
Sachindra, 2006, "Recovery of carotenoids from shrimp waste in organic solvents", Waste Management, 26: 1092-1098.
Saether et al., 1986, "Lipids of North Atlantic krill", J Lipid Res., 27(3):274-85.
Shahidi et al., 1998, "Carotenoid Pigments in Seafoods and Aquaculture" Critical Reviews in Food Science, 38(1): 1-67.
Sidehu et al., 1970, "Biochmical Composition and Nutritive Value of Krill (*Euphausia superb* dana)", J. Sci Food Agr., vol. 21, 293-296.
Simopoulos, 1991, "Omega-3 fatty acids in health and disease and in growth and development", Am. Clin. Nutr. 54:438-63.
Somiya, 1982, "Yellow lens' eyes of a stomiatoid deep-sea fish, *Malacosteus niger*", Proc. R. Soc. Lond., 215: 481-489.
International Search Report, International Patent Application No. PCT/IB2016/000208, dated May 13, 2016, five pages.
Partial International Search Report, International Patent Application No. PCT/IB2016/000326, dated Jun. 15, 2016, six pages.
Database FSTA [Online} International Food Information Service, Frankfurt-Main; Shibata N. "Effect of fishing season on lipid content and composition of Antarctic krill (translated)" Database accession No. FS-1985-04-r-0091, abstract only.
Statement of Grounds and Particulars, Rimfrost AS, filed Jun. 10, 2016, Australian Patent Application No. 2014203179, 21 pages.
Takahashi et al., Prediction of Relative Retention Value of the Individual Molecular Species of Diacyl Glycerolipid on High Performance Liquid Chromatography, Bull. Fac. Fish. Hokkaido Univ. 38(4), 398-404. 1987.
Tanaka, Biosynthesis of 1,2-dieicosapentaenoyl-sn-glycero-3-phosphocholine in Caenorhabditis elegans, Eur. J. Biochem. 263, 189±194 (1999).
Tocher, Chapter 6, Glycerophospholipid metabolism, Biochemistry and molecular biology of fishes, vol. 4, Hochachka and Mommsen (eds.)(1995).
Watanabe et al., Effective Components in Cuttlefish Meal and Raw Krill for Improvement of Quality of Red Seabream Pagrus major Eggs, Nippon Suisan Gakkaishi 57(4):681-694 (1991)("Watanabe").
WHO News and Activities, Bulletin of the World Health Organization, 73(4), pp. 547-551 (1995) ("WHO Bulletin").
Valeri, D., et al., "Visocities of Fatty acids, triglycerides and their binary mixtures," JAOCS 74 (1997) pp. 1221-1226.
CRC 2013-2014, 94th ed., pp. 6-231-6-235.
EP Opposition filed Feb. 13, 2014 by Olympic Seafood AS, EP Patent Application No. EP0871891016.
Brzustowicz, Michael R., et al., "Controlling Membrane Cholesterol Content. A Role for Polyunsaturated (Docosahexaenoate) Phospholipids," Biochemistry (2002), 41, pp. 12509-12519.
Jong-Ho Lee, "A Review: Antioxygenic and Peroxide decomposing Activities of Antarctic Krill Lipids," J. Korean Soc. Food Mutr. 13(3) pp. 326-333 (1984).
Ki Woong Cho, et al., "Lipid and Fatty Acid Composition of the Antarctic Krill *Euphausia superba*," Ocean Research 21(2): 109-116 (1999).
Hvattum, Erlend, et al., "Effect of soybean oil and fish oil on individual molecular species of Atlantic salmon . . . ", Journal of Chromatography B, 748 (2000) 137-149.
Igarashi, Daisuke, et al., "Positional Distribution of DHA and EPA in Phosphatidylcholine and Phosphatidylethanolamine from Different Tissues of Squids," J. Oleo Sci. vol. 50, No. 9 (2001).
Tochizawa, Kaoru, et al., "Effects of Phospholipds Containing Docosahexaenoic Acid on Differentiation and Growth of HL-60 Human Promyelocytic Leukemia Cells," J. Jpn. Oil Chem. Soc. vol. 46, No. 4 (1997).

(56) References Cited

OTHER PUBLICATIONS

Zerouga, Mustapha, et al., "Comparison of phosphatidylcholines containing one or two docosahexaenoic acyl chains on properties of phospholipid monolayers and bilayers," Biochimica et Biophysica Acta 1236 (1995) 266-272.
Eung-Ho Lee, et al., "Studies on the Processing of Krill Sauce," J. Korean Soc. Food Nutr. 13(1) 97-106 (1984).
Hyun-Ku Kim, et al., "Effects of Cooking and Drying Methods on the Polar Lipds Composition of Shrimp," Korean J. Food Sci. Technol. vol. 21, No. 1, pp. 25-30 (1989).
Shon, Mi-Yae, et al., "Effects of Krill and Cadmium on Lipid Composition of Plasma in Cholesterol-Fed Rats," J. Korean Soc. Food Nutr. 23(1), 38-43 (1994).
Summons Materials downloaded from ESPACE on Dec. 16, 2014 for EP Patent Application No. 08 718 910.6.
Yanase, M., "Innovations on the russian method for separating heat coagulated protein from antarctic krill, through autolysis," Bulletin of Tokai Regional Fisheries Research Laboratory, 1974, No. 78, p. 79-84.
Kolakowski and Gajowiecki, "Optimization of autoproteolysis to obtain and edible product 'precipitate' from Antarctic krill," Seafood Science and Technology, pp. 331-336.
EP Opposition filed May 8, 2015 by Olympic Seafood AS, EP Patent No. 2144618, 150 pages.
Allahpichay et al., "Extraction of Growth Promoting Fractions from Non-muscle Krill Meal of Euphausia superba and its Effect on Fish Growth," Bulletin of the Japanese Society of Scientific Fisheries, 1984, 50(5): 821-826.
Notification of Generally Recognized as Safe (GRAS) Determination for Krill Oill; Food and Drug Administration. Center for Food Safety and Applied Nutrition. p. 1-49, Dec. 14, 2010.
Takaichi et al., 2003, "Fatty Acids of astaxanthin esters in krill determined by mild mass spectrometry", Comparative Biochemistry and Physiology Part B, Biochemistry and Molecular Biology, Elsevier, Oxford, vol. 136, Jan. 1, 2003, p. 317-322.
Tanaka et al., 2004, "Extraction of Phospholipids from Salmon Roe with Supercritical Carbon Dioxide and an Entrainer", J. Oleo Sci, 53(9): 417-424.
Tanaka et al., 2005, "Extraction of Phospholipids from Unused Natrual Resources with Supercritical Carbon Dioxide and an Entrainer", Journal of Oleo Science, vol. 54(11): 569-576.
Todoric et al., 2006, "Adipose tissue inflammation induced by high-fat diet in obese diabetic mice is prevented by n-3 polyunsaturated fatty acids", Diabetologia, 49(9): 2109-2119.
Tou et al., 2007, "Krill for human consumption: nutritional value and potential health benefits.", Nutrition Rev 65(2):63-77.
Trayhurn et al., 2004, "Adipokines: inflammation and the pleiotropic role of white adipose tissue", Br. J. Nutrition, 92(3): 347-355.
Trebble et al., 2003, "Inhibition of tumour necrosis factor-alpha and interleukin 6 production by mononuclear cells following dietary fish-oil supplementation in healthy men and response to antioxidant co-supplementation", Br. J. Nutrition, 90(2): 405-412.
Ukkola et al., 2002, "Adiponectin: a link between excess adiposity and associated comorbidities?", J. Mol. Med., 80(11): 696-702.
Van Der Veen et al., 1971 "The Lipids of Krill (*Euphausia* Species) and Red Crab (*Pleuroncodes planipes*)", Lipids, 6(7): 481-485.
Virtue, et al. 1996, Reproductive trade-off in male Antarctic krill, *Euphausia superba*, Marine Biology, vol. 126, No. 3, pp. 521-527.
Yamaguchi et al., 1983, "The Composition of Carotenoid Pigments in the Antarctic Krill *Euphausia superba*", Bulletin of the Japanese Society of Scientific Fisheries, 49(9): 1411-1415.
Yamaguchi et al., 1986, "Supercritical Carbon Dioxide Extraction of Oils From Antarctic Krill," Journal of Agricultural and Food Chemistry, vol. 34, pp. 904-907.
Yanase M; 1974, "Modification of a Russian method for separation of heat-coagulated protein from Antarctic krill", Database FSTA (online); International Food Information Service (IFIS); Frankfurt-Main, DE.

Yen et al., 1994, "Effect of dietary omega-3 and omega-6 fatty acid sources on PUVA-induced cutaneous toxicity and tumorogenesis in the hairless mouse", Arch. Dermatol. Res., 286(6): 331-6.
Database WPI Week 200682, Thomson Scientific, London, GB, 2006.
Yanase, M., "Modification of Russian Method for Separating Heat Congulated Protein from Antarctic Krill," Bull. Tokai Reg. Fish. Res. Lab, 78: 79-84 (1974).
Sikorski, E., "The Utilization of Krill For Food," Food Process Eng., 1:845-855 (1980).
Budzinskli, E., et al., "Possibilities of processing and marketing of products made from Antarctic Krill", FAO Fish. Tech. Pap. (268) 46 pages (1985) (Budzinski).
Bunea R., et al.., "Evaluation of the Effects of Neptune Krill Oil on the Clinical Course of Hyperlipidemia," Alternative Medicine Review, Thorne Research Inc., Sandpoint, US, vol. 9, No. 4, Jan. 1, 2004.
Gordeev, K.Y., et al. "Fatty Acid Composition of the Main Phospholipids of the Antarctic Krill, *Euphausia superba*," Khim. Prirod. Soed. 2 (1990), pp. 181-187.
Dec. 8, 2011 Office Action, KR Patent Application No. 10-2010-7006897 and its English translation.
JP Office Action dated Feb. 23, 2012, JP Patent Application No. 2010-522444 (and English translation).
CN Office Action dated Apr. 27, 2012, JP Patent Application No. 200880112125.6 (and English translation).
Fricke, et al., Lipid, Sterol and Fatty Acid Composition of Antarctic Krill (*Euphausia superba* Dana), Lipids (1984) 19(11): 821-827.
Fricke, et al., 1-O-Alkylglycerolipids in Antarctic Krill (*Euphausia superba* Dana), Comp. Biochem. Physiol. (1986) 85B(1): 131-134.
Gordeev, K.Y., et al. "Fatty Acid Composition of the Main Phospholipids of the Antarctic Krill, *Euphausia superba*," Chem. Nat. Cmpds. (1990) 26(2), pp. 143-147.
Grantham (1977) Southern Ocean Fisheries Survey Programme, FAO Rome, GLO/SO/77/3: 1-61.
Raventos et al., Application and Posssibilities of Supercritical CO2 Extraction in Food Processing Industry: An Overview, Food Science and Technology International (2002) 8: 269-284.
Tanaka, T., et al., Platelet-activating Factor (PAF)-like Phospholoipds Formed during Peroxidation of Phosphatidylcholines from Different Foodstuffs, Biosci. Biotech. Biochem. (1995) 59 (8), pp. 1389-1393.
Winther, et al., Elucidation of Phosphatidylcholine Composition in Krill Oil Extracted from Euphausia superba, Lipids (2011) 46: 25-36.
"Neptune Technologies & Bioressources Soon to Obtain a Major Patent in Over 30 Countries" ("2001 Press Release,").
Action Closing Prosecution, '348 patent.
Apr. 2, 2012 Response to Office Action, '351 patent.
Balassa et al., Microencapsulation in the Food Industry, Critical Reviews in Food Technology, 2:2, 245-265 (1971) ("Balassa").
Bell and Dick, Molecular Species Composition of the Major Diacyl Glycerophospholipids from Muscle, Liver, Retina and Brain of Cod (*Gadus morhua*), Lipids, vol. 26, No. 8, pp. 565-573 (1991) ("Bell and Dick").
Bell, Molecular Species Analysis of Phosphoglycerides from the Ripe Roes of Cod, Lipids, vol. 24, No. 7 (1989).
Bell, Molecular Species Composition of Phosphatidylcholine from Crypthecodinium cohnii in Relation to Growth Temperature Lipids 25, 115-118 (1990).
Bergelson (ed.), Lipid Biochemical Preparations, Chapter I.1, pp. 1-13 (1980).
Bottino N.R., "Lipid Composition of Two Species of Antarctic Krill: *Euphausia superba* and *E. crystallorophias*," Comp. Biochem. Physiol., 1975, vol. 50B, pp. 479-484.
Buchi R-220 Rotovapor® Manual.
Buda, Structural order of membranes and composition of phospholipids in fish brain cells during thermal acclimatization, Proc. Natl. Acad. Sci. USA vol. 91, pp. 8234-8238, Aug. 1994.
Certificate of translation of Ex. 1072: Fisheries Agency, General Report on Research and Development of Techniques in Processing and Utilization of Marine Products, Chapter 6, Development of technology for recovery of valuable substances (astaxanthin) from krill, by Takao Fujita, pp. 273-307 (Mar. 1985); Japanese language document.

(56) References Cited

OTHER PUBLICATIONS

Certificate of translation of Ex. 1074: Japanese Patent No. 60-153779, entitled "Nutritional Supplement".
Certificate of translation of Ex. 1076: Japanese Patent Publication No. H08-231391, entitled "Medicine for Improvement of Dementia Symptoms".
Certification of translation of Ex. 1070: Japanese Unexamined Patent Application Publication No. 02-215351.
Certified translation of Ex. 1070: Japanese Unexamined Patent Application Publication No. 02-215351, titled Krill Phospholipids Fractioning Method ("Maruyama"); Certification of Translation provided as Ex. 1071.
Certified translation of Ex. 1072: Fisheries Agency, General Report on Research and Development of Techniques in Processing and Utilization of Marine Products, Chapter 6, Development of technology for recovery of valuable substances (astaxanthin) from krill, by Takao Fujita, pp. 273-307 (Mar. 1985) ("Fujita") ; Certificate of Translation provided as Ex. 1073.
Certified translation of Ex. 1074: Japanese Patent No. 60-153779, entitled "Nutritional Supplement" ("Fukuoka"); Certificate of Translation provided as Ex. 1075.
Certified translation of Ex. 1076: Japanese Patent Publication No. H08-231391, entitled "Medicine for Improvement of Dementia Symtoms" ("Yasawa"); Cerificate of Translation provided as Ex. 1077.
Declaration of Bjorn Ole Haugsgjerd in support of Inter Partes Review of U.S. Pat. No. 8,278,351.

\* cited by examiner

LIPID COMPOSITIONS

CROSS-REFERENCE TO RELATED APPLICATIONS

This application is a continuation of U.S. patent application Ser. No. 15/040,347, filed Feb. 10, 2016, allowed as U.S. Pat. No. 10,864,223, which claims the benefit U.S. Provisional Patent Application No. 62/114,811 filed Feb. 11, 2015, the contents of which are incorporated by reference in their entireties.

FIELD OF THE INVENTION

The present invention provides improved processes for extracting and preparing lipids from biological sources for use in pharmaceuticals, nutraceuticals and functional foods, as well as the compositions resulting therefrom.

BACKGROUND OF THE INVENTION

Krill oil is one of the fastest growing nutraceutical products. Krill oil may be extracted from any species of krill, but is most generally extracted from the Antarctic krill *Euphausia superba*. Krill oil provides a bioavailable source of omega-3 fatty acids such as eicosapentaenoic acid (EPA) and docosahexaenoic acid (DHA) as well as the antioxidant astaxanthin. Krill oil is generally characterized as containing substantial amounts of phospholipids as well as triglycerides.

WO2008/117062 describes extraction of krill oil from krill meal using polar solvents and extractions processes such as supercritical fluid extraction. One problem with krill oil extracted from krill meal is that the oil generally has a high viscosity which makes formulation into preferred delivery forms such as gel capsules difficult. The cause of the high viscosity has not been previously described.

WO2009/027692 and WO2010/097701 describe processes for making a krill protein-lipid coagulate and extraction of an oil from the coagulate. The resulting oils can have a low viscosity. However, the coagulate can be difficult to store and ship due to a high moisture content.

Little work has been done to discover processes for extracting low viscosity krill oil from the more readily available krill meal. Thus, what is need in the art are processes for extracting a low viscosity krill oil from krill meal and the low viscosity krill oils resulting from those processes.

SUMMARY OF THE INVENTION

The present invention provides improved processes for extracting and preparing lipids from biological sources for use in pharmaceuticals, nutraceuticals and functional foods.

Accordingly, in the some embodiments, the present invention provides a desalted krill lipid composition comprising: from about 30% to 50% w/w phospholipids w/w and from about 32% to 52% w/w triglycerides; and wherein the composition has one or more of the following properties: a) the composition comprises from about 3% w/w to 13% w/w free fatty acids; b) the composition comprises from about 0.5% w/w to 5% w/w lysophospholipids; c) the composition comprises less than about 0.2% w/w inorganic salts; d) the composition comprises less than about 2 mg N/100 g; e) the composition comprises less than about 2 ppm $Cu^{++}$; f) the composition comprises less than about 3 ppm total arsenic; g) the composition comprises from about 0.01% to about 1% w/w ethyl esters; h) the composition is characterized in having a conductivity of less than about 20 µS/cm when measured with 5% dry matter in 95% ethanol; i) the composition is characterized in having a viscosity of from about 100 to 400 mPas at 25° C.; and (j) the composition comprises from about 20 ppm to about 2000 astaxanthin esters. In some embodiments, the compositions have 2 or more of properties (a) to (j). In some embodiments, the compositions have 3 or more of properties (a) to (j). In some embodiments, the compositions have 4 or more of properties (a) to (j). In some embodiments, the compositions have 5 or more of properties (a) to (j). In some embodiments, the compositions have 6 or more of properties (a) to (j). In some embodiments, the compositions have 7 or more of properties (a) to (j). In some embodiments, the compositions have 8 or more of properties (a) to (j). In some embodiments, the compositions have 8 or more of properties (a) to (j). In some embodiments, the compositions have all of properties (a) to (j). In some embodiments, the compositions have at least properties (c) and (i). In some embodiments, the compositions have at least property (h). In some embodiments, the compositions have at least properties (e) and (f). In some embodiments, the compositions have at least property (d). In some embodiments, the compositions have at least properties (c), (d), (e), (f), (h) and (i).

In some embodiments, the present invention provides krill phospholipid concentrates comprising: from about 50% to 85% w/w phospholipids and from about 5% to 35% w/w triglycerides; and wherein the composition has one or more of the following properties: (a) the composition comprises from about 2% w/w to 13% w/w free fatty acids; (b) the composition comprises from about 0.5% w/w to 10% w/w lysophospholipids; (c) the composition comprises less than about 0.2% w/w inorganic salts; (d) the composition comprises less than about 2 mg N/100 g; (e) the composition comprises less than about 2 ppm $Cu^{++}$; (f) the composition comprises less than about 3 ppm total arsenic; (g) the composition comprises from about 0.01% to about 1% w/w ethyl esters; (h) the composition is characterized in having a conductivity of less than about 20 µS/cm when measured with 5% dry matter in 95% ethanol; (i) the composition is characterized in having a viscosity of from about 600 to 1600 mPas at 35° C.; and (j) the composition has comprises less than about 100 ppm astaxanthin esters. In some embodiments, the compositions have 2 or more of properties (a) to (j). In some embodiments, the compositions have 3 or more of properties (a) to (j). In some embodiments, the compositions have 4 or more of properties (a) to (j). In some embodiments, the compositions have 5 or more of properties (a) to (j). In some embodiments, the compositions have 6 or more of properties (a) to (j). In some embodiments, the compositions have 7 or more of properties (a) to (j). In some embodiments, the compositions have 8 or more of properties (a) to (j). In some embodiments, the compositions have 9 or more of properties (a) to (j). In some embodiments, the compositions have all of properties (a) to (j). In some embodiments, the compositions have at least properties (c) and (i). In some embodiments, the compositions have at least property (h). In some embodiments, the compositions have at least properties (e) and (f). In some embodiments, the compositions have at least property (d). In some embodiments, the compositions have at least properties (c), (d), (e), (f), (h) and (i).

In some embodiments, the present invention krill neutral lipid compositions comprising: from about 70% to 95% w/w triglycerides and from about 2% to 20% w/w phospholipids; and wherein the composition has one or more of the following properties: (a) the composition comprises from about 0.5% w/w to 10% w/w free fatty acids; (b) the composition comprises from about 0.1% w/w to 2% w/w lysophospholipids; (c) the composition comprises less than about 0.2% w/w inorganic salts; (d) the composition comprises less than about 2 mg N/100 g; (e) the composition comprises less than about 2 ppm $Cu^{++}$; (f) the composition comprises less than about 3 ppm total arsenic; (g) the composition comprises from about 0.01% to about 1% w/w ethyl esters; (h) the composition is characterized in having a conductivity of less than about 20 µS/cm when measured with 5% dry matter in 95% ethanol; i) the composition is characterized in having a viscosity of less than about 200 mPas at 25° C.; j) the composition comprises greater than about 300 ppm astaxanthin esters. In some embodiments, the compositions have 2 or more of properties (a) to (j). In some embodiments, the compositions have 3 or more of properties (a) to (j). In some embodiments, the compositions have 4 or more of properties (a) to (j). In some embodiments, the compositions have 5 or more of properties (a) to (j). In some embodiments, the compositions have 6 or more of properties (a) to (j). In some embodiments, the compositions have 7 or more of properties (a) to (j). In some embodiments, the compositions have 8 or more of properties (a) to (j). In some embodiments, the compositions have 9 or more of properties (a) to (j). In some embodiments, the compositions have all of properties (a) to (j). In some embodiments, the compositions have at least properties (c), (i) and (j). In some embodiments, the compositions have at least property (h). In some embodiments, the compositions have at least properties (e) and (f). In some embodiments, the compositions have at least property (d). In some embodiments, the compositions have at least properties (c), (d), (e), (f), (h), (i) and (j).

In some embodiments, the present invention provides a crude krill lipid compositions comprising: from about 30% to 50% w/w phospholipids w/w and from about 26% to 46% w/w triglycerides; and wherein the composition has one or more of the following properties: (a) the composition comprises from about 1% w/w to 7% w/w diglycerides; (b) the composition comprises from about 2% w/w to 12% w/w free fatty acids; (c) the composition comprises from about 1% w/w to 7% w/w cholesterol; (d) the composition comprises from about 0.1% w/w to 2% w/w cholesterol esters, more preferably from about 0.2% w/w to about 1.0% w/w cholesterol esters; (e) the composition comprises from about 0.5% w/w to 5% w/w inorganic salts; (f) the composition comprises from about 0.5% w/w to 5% w/w tertiary amines. In some embodiments, the compositions have 2 or more of properties (a) to (f). In some embodiments, the compositions have 3 or more of properties (a) to (f). In some embodiments, the compositions have 4 or more of properties (a) to (f). In some embodiments, the compositions have 5 or more of properties (a) to (f). In some embodiments, the compositions have all of properties (a) to (f). In some embodiments, the compositions have at least properties (a), (c) and (e).

In some embodiments, the present invention provides concentrated krill astaxanthin compositions comprising: from about 400 to 4000 ppm astaxanthin esters and greater than about 98% krill neutral lipids.

In some embodiments, the present invention provides an oral delivery vehicle comprising the compositions described above. In some embodiments, the vehicle is a soft gel capsule. In some embodiments, the present invention provides a functional food, nutritional supplement, dietary supplement or medical food comprising the compositions described above. In some embodiments, the composition may comprise a second nutraceutical ingredient in addition to the krill lipid composition. In some embodiments, the present invention provides a pharmaceutically acceptable carrier and a krill lipid composition as described above.

DEFINITIONS

As used herein, "phospholipid" refers to an organic compound that has two fatty acid moieties attached at the sn-1 and sn-2 positions of glycerol, and contain a head group linked by a phosphate residue at the sn-3 position of the glycerol. Exemplary headgroup moieties include choline, ethanolamine, serine and inositol. Phospholipids include phosphatidylcholine, phosphatidylserine, phosphatidylethanolamine, phosphatidylinositol and phosphatidic acid. The fatty acid moiety is the portion of the fatty acid molecule that is bound at the sn-1 or sn-2 position, for example by an ester or ether linkage. When the fatty acid moiety is a fatty acyl, the aliphatic chain of the fatty acyl is attached via an ester linkage and when the fatty acid moiety is an aliphatic chain of a fatty acid, the aliphatic chain is attached via an ether linkage. When a particular fatty acid is mentioned in connection with a phospholipid of the invention (e.g., EPA or DHA) it should therefore be taken as a reference to the relevant fatty acyl group or to its aliphatic chain.

As used herein, the term "ether phospholipid" refers to a phospholipid wherein the fatty acid moiety at one of the sn-1 or sn-2 positions is an aliphatic chain of a fatty acid attached via an ether linkage. Ether phospholipids include, for example, alkylacylphosphatidylcholine, alkylacylphosphatidylethanolamine and alkylacylphosphatidylserine.

As used herein, the term "long chain polyunsaturated fatty acid" refers to a fatty acid having 20 or more carbons and which is unsaturated at two or more bonds.

As used herein, the term omega-3 fatty acid refers to polyunsaturated fatty acids that have the final double bond in the hydrocarbon chain between the third and fourth carbon atoms from the methyl end of the molecule. Non-limiting examples of omega-3 fatty acids include, 5,8,11,14,17-eicosapentaenoic acid (EPA), 4,7,10,13,16,19-docosahexanoic acid (DHA) and 7,10,13,16,19-docosapentanoic acid (DPA).

As used herein, the term "physiologically acceptable carrier" refers to any carrier or excipient commonly used with oily pharmaceuticals. Such carriers or excipients include, but are not limited to, oils, starch, sucrose and lactose.

As used herein, the term "oral delivery vehicle" refers to any means of delivering a pharmaceutical orally, including, but not limited to, capsules, pills, tablets and syrups.

As used herein, the term "food product" refers to any food or feed suitable for consumption by humans, non-ruminant animals, or ruminant animals. The "food product" may be a prepared and packaged food (e.g., mayonnaise, salad dressing, bread, or cheese food) or an animal feed (e.g., extruded and pelleted animal feed or coarse mixed feed). "Prepared food product" means any pre-packaged food approved for human consumption.

As used herein, the term "foodstuff" refers to any substance fit for human or animal consumption.

As used herein, the term "functional food" refers to a food product to which a biologically active supplement has been added.

As used herein, the term "infant food" refers to a food product formulated for an infant such as formula.

As used herein, the term "elderly food" refers to a food product formulated for persons of advanced age.

As used herein, the term "pregnancy food" refers to a food product formulated for pregnant women.

As used herein, the term "nutritional supplement" refers to a food product formulated as a dietary or nutritional supplement to be used as part of a diet.

As used herein, the term w/w (weight/weight), unless otherwise specified, refers to the amount of a given substance in a composition on a weight basis and is expressed as a percentage of the total composition weight. For example, a composition comprising 50% w/w phospholipids means that the mass of the phospholipids is 50% of the total mass of the composition (i.e., 50 grams of phospholipids in 100 grams of the composition, such as an oil). When solvent concentration is designated throughout the specification, the concentration refers to the weight percent of solvent in the designated solvent solution. As a non-limiting example, 96% ethanol comprises 96% ethanol and 4% water. As another non-limiting example, when the specification describes a lipid solution as comprising 20% w/w dry matter and that the solvent is 95% ethanol, this means that 100 g of the solution comprises a total of 20 grams dry matter and 80 g of 95% ethanol.

As used herein, the term "krill meal" refers to dried powder prepared from krill and having a moisture content of from about 3% to about 15%.

DETAILED DESCRIPTION OF THE INVENTION

The present invention provides improved processes for extracting and preparing lipids from biological sources for use in nutraceuticals, pharmaceuticals and functional foods as well as the compositions resulting therefrom. In particularly preferred embodiments, the biological source is krill, for example *Euphausia superba* or *Euphausia pacifica*.

One of the primary problems with existing krill oil is that oil is viscous and difficult to fill into preferred delivery vehicles such as gel capsules. Other problems currently associated with krill oil production includes products with compromised purity, smell and taste, processes with low mass yield from the raw material, and products with lower than desirable astaxanthin and phospholipid content. The present inventors have unexpectedly found that impurities in krill oil made by commercial extraction processes, rather than phospholipid content, is responsible for problems associated with viscosity. In particular, removal of hexane insoluble components such as rock salt, from the krill oil results in krill oil with reduced viscosity, improved handling properties, better stability, and improved organoleptic properties.

A related problem is that current processes for extracting lipids from krill are often inefficient. In order to avoid extraction of contaminants that effect krill oil quality, efficiency of extraction of lipids is often sacrificed. Thus, in order to extract a high quality krill oil, current processes utilize gentle extraction techniques that leave a substantial amount of lipids in the starting krill material.

The present invention addresses these problems by first utilizing a high efficiency or high yield process for extraction of crude krill lipid composition from a krill starting material, such as krill meal. In some embodiments, the high yield extraction extracts from about 70 to 90% w/w of the total available lipids in the krill biomass compared to about a 66% yield seen in previous extraction methods utilizing protic solvents. The crude krill lipid composition is then desalted to provide a desalted krill lipid composition containing from about 30% to 50% w/w phospholipids. The desalted krill lipid compositions are useful as nutritional supplements, dietary supplements, and in functional foods. The desalted krill lipid compositions also serve as an excellent material for the production of krill phospholipid concentrates and neutral lipid concentrates containing high levels of astaxanthin. As described below, the present invention further provides processes for the fractionation and separation of krill phospholipid concentrates and krill neutral lipid concentrates by controlled fractionation of the desalted krill lipid compositions with an alcohol followed by cryocentrifugation. The end result is high quality krill phospholipid concentrate compositions comprising from about 50% and up to about 85% phospholipids w/w and krill neutral lipid concentrate compositions with high levels of astaxanthin. Astaxanthin may be further purified from the krill neutral lipid concentrate compositions. The krill neutral lipid concentrate compositions of purified astaxanthin may be blended with the krill phospholipid concentrate compositions to provide krill lipid compositions with desired amount of phospholipids and astaxanthin.

The combination of these process steps provides an efficient, flexible platform for the production of high quality products from a krill starting material. The high quality products are generally characterized by having a low viscosity, little or no smell, improved taste, improved stability, low lysophospholipid content, and low levels of unwanted materials or contaminants such as solvents, copper and other metallic pro-oxidants, total arsenic (including organic and inorganic arsenic), trimethylamine oxide, and ethyl esters.

The remainder of the description is subdivided as follows: 1) Starting materials; 2) Solvent extraction from krill meal; 3) Desalting; 4) Lipid and astaxanthin concentration; 5) Formulation of krill phospholipid compositions; and 6) Uses of krill phospholipid compositions.

1. Starting Materials

The present invention is not limited to the use of any particular biological starting material. The biological starting material may preferably be or be produced from an algal biomass, plant biomass or marine animal biomass. In preferred embodiments, marine animal biomasses are utilized as the starting material. Suitable marine animal biomasses include, but are not limited to, krill, crabs, Calanus, plankton, eggs, crayfish, shrimp, fish, especially herring, molluscs (including cephalopods such as squid), plants and algae. The biological starting material can be either fresh or frozen, or can be a material produced from an algal, plant or marine animal biomass such as a meal, powder, hydrolysate, or coagulate (paste). The paste may be a wet paste or a dried paste. In some preferred embodiments, the biological starting material is a krill material, for example a krill meal, krill hydrolysate, krill coagulate, or fresh or frozen krill. Any species of krill may be utilized. In preferred embodiments, the krill is *Euphausia superba* or *Euphausia pacifica*.

In some particularly preferred embodiments, the biological starting material is a krill meal. Krill meal can be preferably be made by any standard marine meal process. In general, the krill meal is produced by cooking freshly caught krill at low temperature (approximately 80-85° C.) and drying to reduce the moisture content to approximately 5 to 8% and then grinding. In embodiments where the product is intended for human consumption, it is preferable to pack and store the meal under nitrogen without the addition of antioxidants.

Accordingly, the processes of the present invention may be used with a wide variety of starting materials. The remainder of the discussion of the processes generally refer to the use of krill meal as the starting material. However, it will be understood that any of the starting materials considered herein may be substituted for krill meal in the described processes.

2. Solvent Extraction from Krill Meal

In the first step of the extraction process, the krill meal is mixed with a suitable solvent to extract lipids from the meal. In contrast to prior art methods, the present invention utilizes conditions which preferably extract the maximum amount of lipids from the krill meal at the cost of an increased amount of contaminants in the initial solvent extract. In preferred embodiments, the solvent is an organic protic solvent, however other solvents known for use in extraction of food grade lipids may also be used such as acetone, hexane, etc. Suitable organic protic solvents include, but are not limited to, n-butanol, n-propanol, isopropanol, nitromethane, ethanol, and methanol. In particularly preferred embodiments, the protic solvent is ethanol.

In preferred embodiments, the concentration of the protic solvent used in the initial solvent extraction step is at least 90%, or preferably from about 94% to 98%, more preferably from about 95% to 97%, and is most preferably about 96% (e.g., 96% ethanol or methanol).

In some embodiments, the protic solvent is mixed with the biological starting material at a ratio of protic solvent: biological starting material of about 1:1 to 10:1, preferably about 3:1 to 6:1, more preferably about 4:1 to 5:1, and most preferably about 4.4:1.

In preferred embodiments, the biological starting material is extracted with protic solvent at a temperature of from about 5° C. to 65° C., from about 20° C. to about 60° C., preferably from about 30° C. to 50° C., more preferably from about 30° C. to 50° C., and most preferably at about 40° C. In some embodiments, the extraction time (i.e., the amount of time the biological starting material is in contact with the solvent) is from about 10 minutes to about 2 hours, preferably from about 15 minutes to 60 minutes, more preferably from about 20 minutes to about 45 minutes, and most preferably about 30 minutes.

Following the extraction step, a crude krill lipid solution containing the soluble lipids from the krill meal is separated from the solvent/krill meal mixture, for example by decantation and or filtration. The insoluble material, comprising proteins and other useful materials is then dried to recover ethanol. The remaining protein-rich meal product may subsequently be used in food products, protein supplements, animal feeds and the like. In some embodiments, the decanted solution containing soluble lipids has a dry matter content of from about 4% to 9% w/w, preferably from about 5.5% to 7.5% w/w, and most preferably from about 6% to 7% w/w, where w/w refers to the weight of dry matter as a percent of the total solution weight. In preferred embodiments, the dry matter consists essentially of crude krill lipids, and preferably has a lipid content of greater than 90%, 95%, 96%, 97%, 98% or 99% w/w, wherein w/w refers to the weight of lipids a percent of the total dry matter weight.

The composition of the crude krill lipids may be preferably characterized as follows. In some embodiments, the crude krill lipids preferably comprise from about 30% w/w to 50% w/w phospholipids, more preferably from about 35% w/w to about 45% w/w phospholipids, and most preferably about 40% w/w phospholipids, wherein w/w refers to the weight of the phospholipids as a percent of the total crude krill lipid weight. In some embodiments, the crude krill lipids preferably comprise from about 26% w/w to 46% w/w triglycerides, more preferably from about 31% w/w to about 41% w/w triglycerides, and most preferably about 36% w/w triglycerides, wherein w/w refers to the weight of the triglycerides as a percent of the total crude krill lipid weight. In some embodiments, the crude krill lipids preferably comprise from about 1% w/w to 7% w/w diglycerides, more preferably from about 1.5% w/w to about 4.5% w/w diglycerides, and most preferably about 3% w/w diglycerides, wherein w/w refers to the weight of the diglycerides as a percent of the total crude krill lipid weight. In some embodiments, the crude krill lipids preferably comprise from about 2% w/w to 12% w/w free fatty acids, more preferably from about 4.5% w/w to about 9.5% w/w free fatty acids, and most preferably about 7% w/w free fatty acids, wherein w/w refers to the weight of the free fatty acids as a percent of the total crude krill lipid weight. In some embodiments, the crude krill lipids preferably comprise from about 1% w/w to 7% w/w cholesterol, more preferably from about 1.5% w/w to about 4.5% w/w cholesterol, and most preferably about 3% w/w cholesterol, wherein w/w refers to the weight of the cholesterol as a percent of the total crude krill lipid weight. In some embodiments, the crude krill lipids preferably comprise from about 0.1% w/w to 2% w/w cholesterol esters, more preferably from about 0.2% w/w to about 1.0% w/w cholesterol esters, and most preferably about 0.5% w/w cholesterol esters, wherein w/w refers to the weight of the cholesterol esters as a percent of the total crude krill lipid weight. In some embodiments, the crude krill lipids preferably comprise from about 0.5% w/w to 5% w/w inorganic salts, more preferably from about 0.8% w/w to about 3.2% w/w inorganic salts, and most preferably about 1.2% to 2.8% w/w inorganic salts, wherein w/w refers to the weight of the inorganic salts as a percent of the total crude krill lipid weight. In some embodiments, the crude krill lipids preferably comprise from about 0.5% w/w to 5% w/w tertiary amines (e.g., trimethylamine oxide (TMAO) and other tertiary amines), more preferably from about 0.8% w/w to about 3.2% w/w tertiary amines, and most preferably about 1.2% to 2.8% w/w tertiary amines, wherein w/w refers to the weight of the tertiary amines as a percent of the total crude krill lipid weight. In some embodiments, the teritiary amines are TMAO.

3. Desalting

In some embodiments, the crude krill lipid solution is desalted to remove hexane insoluble materials such as insoluble inorganic salts (e.g., NaCl with small or trace amounts of KCl and/or $AlCl_3$) as well as unwanted compounds such as trimethylamine oxide, and metals such as copper and arsenic.

In some embodiments, the crude krill lipid solution is desalted by evaporating the solvent from crude krill lipid solution to provide a crude krill lipid composition and then subjecting the crude krill lipid composition to repeated washes with an aqueous solvent. Suitable aqueous solvents include, but are not limited to, ethanol blended with water or deionized water so that the ethanol concentration is from about 40% to 70%, preferably about 50% to 60%. In these embodiments, the crude krill lipid composition is mixed with the solvent, the lipid phase is recovered, and the aqueous phase is decanted. The washing step may be repeated as needed, for example 1, 2, 3, 4, 5 or more times. The ration of aqueous solvent: crude krill lipid composition is preferably from about 1:1 to 1:5 for each wash step, more preferably from about 1:1 to 2.5:1, and most preferably about 1:1.7.

In some embodiments, the crude lipid solution is desalted by chromatography. Suitable chromatographic media include silica gel media, including but not limited to spherical silica gels and derivatized silica gels such as C8 (octyl functionalized silica) and C18 (octadecyl functional silica)

and ion exchange resins such as Dowex™ resins. In embodiments where chromatography is utilized, the crude krill lipids are preferably applied to the chromatographic medium in a protic solvent, preferably the same solvent used in the initial extraction (e.g., ethanol). Standard column chromatography methods may be utilized, however, moving bed chromatography or simulated moving bed chromatography apparatuses may preferably be utilized.

In some embodiments, a krill oil extract comprising polar lipids, neutral lipids, trimethylamine oxide (TMAO), salt and astaxanthin is desalted by simulated moving bed chromatography. In some preferred embodiments, the krill extract is diluted in an effective amount of solvent to a concentration of between about 2 and about 7 wt-% on a dry basis in the solvent to provide a desalter feed stream. In some embodiments, the solvent is preferably a mixture of ethanol and water having an ethanol to water ratio of from about 99:1 to about 95:5. In some embodiments, the desalter feed stream is introduced to at least one of a plurality of desalting stages in a krill oil simulated moving bed desalting zone, each desalting stage comprising a first column containing a cation exchange resin having a top and a bottom and a second column containing an anion exchange resin having a top and a bottom, and the bottom of the first column being in fluid communication with the top of the second column, wherein at least a portion of the desalting stages are active desalting stages, and at least one desalting stage is undergoing desalting regeneration and withdrawing from one or more active desalting stage a desalted lipid rich stream being essentially free of TMAO and salt. In some embodiments, solvent is preferably recovered from the desalted lipid rich stream to provide desalted krill lipids. These processes are described in more detail in co-pending U.S. application Ser. No. 14/619,102, which is incorporated herein by reference in its entirety.

The composition of the desalted krill lipids on a dry matter basis may be preferably characterized as follows. In some embodiments, the desalted krill lipids preferably comprise from about 30% w/w to 50% w/w phospholipids, more preferably from about 35% w/w to about 45% w/w phospholipids, and most preferably about 40% w/w phospholipids, wherein w/w refers to the weight of the phospholipids as a percent of the total desalted kill lipid weight. In some embodiments, the desalted krill lipids preferably comprise from about 32% w/w to 52% w/w triglycerides, more preferably from about 36% w/w to about 48% w/w triglycerides, and most preferably about 42% w/w triglycerides, wherein w/w refers to the weight of the triglycerides as a percent of the total desalted krill lipid weight. In some embodiments, the desalted krill lipids preferably comprise from about 3% w/w to 13% w/w free fatty acids, more preferably from about 5% w/w to about 11% w/w free fatty acids, and most preferably about 8% w/w free fatty acids, wherein w/w refers to the weight of the free fatty acids as a percent of the total desalted krill lipid weight. In some embodiments, the desalted krill lipids preferably comprise from about 0.5% w/w to 5% w/w lysophospholipids, more preferably from about 0.8% w/w to about 3.2% w/w lysophospholipids, and most preferably about 1.2% to 2.8% w/w lysophospholipids, wherein w/w refers to the weight of the lysophospholipids as a percent of the total desalted krill lipid weight. In some embodiments, the desalted krill lipids preferably comprise less than about 1% w/w inorganic salts, more preferably less than about 0.5% w/w inorganic salts, even more preferably less than about 0.2% w/w w/w inorganic salts, and most preferably less than about 0.1% w/w inorganic salts, wherein w/w refers to the weight of the inorganic salts as a percent of the total desalted krill lipid weight. In some embodiments, the desalted krill lipids preferably comprise less than about 5 mg N/100 g, more preferably less than about 3 mg N/100 g, even more preferably less than about 2 mg N/100 g, and most preferably less than about 1 mg N/100 g, where the N content serves as a proxy for trimethylamine oxide (TMAO) content. In some embodiments, the desalted krill lipids comprise less than about 10 ppm copper ($Cu^{++}$), more preferably less than about 5 ppm $Cu^{++}$, even more preferably less than about 2 ppm $Cu^{++}$, and most preferably less than about 1 ppm $Cu^{++}$. In some embodiments, the desalted krill lipids comprise less than about 10 ppm total arsenic ($As^{3+}$, organic and inorganic), more preferably less than about 5 ppm total arsenic, even more preferably less than about 3 ppm total arsenic, and most preferably less than about 1 ppm total arsenic. In some embodiments, the desalted krill lipids preferably comprise from about 0.01% to 2% w/w ethyl esters, more preferably from about 0.01% to about 1.5% w/w ethyl esters, and most preferably from about 0.01% to about 1% w/w ethyl esters, wherein w/w refers to the weight of the ethyl esters as a percent of the total desalted krill lipid weight. In some embodiments, the krill phospholipid concentrate preferably comprise less than about 5%, 4%, 3% or 2% w/w ethyl esters down to a lower limit of 0.01% ethyl esters (i.e., between 5% and 0.01% w/w ethyl esters, between 4% and 0.01% w/w ethyl esters, between 3% and 0.01% w/w ethyl esters, or between 2% and 0.01% w/w ethyl esters), more preferably less than about 1.5% w/w ethyl esters, and most preferably less than about 1% w/w ethyl esters, wherein w/w refers to the weight of the ethyl esters as a percent of the total desalted krill lipid weight. In some embodiments, the desalted krill lipids have a conductivity of less than about 50 μS/cm when measured with 5% dry matter in 95% ethanol, more preferably a conductivity of less than about 30 μS/cm when measured with 5% dry matter in 95% ethanol, and most preferably a conductivity of less than about 20 μS/cm when measured with 5% dry matter in 95% ethanol. In some embodiments, the desalted krill lipids have a viscosity of from about 50 to 800 mPas at 25° C., more preferably from about 100 to 400 mPas at 25° C., and most preferably 180 to 340 mPas at 25° C. In some embodiments, the desalted krill lipid compositions have a pH of from about 6.7 to 8.3 when measured in 95% ethanol.

4. Lipid and Astaxanthin Concentration

In some embodiments, the present invention provides methods for concentrating lipids (e.g., neutral lipids or polar lipids such as phospholipids) and astaxanthin in a solution. While the methods are described in reference to the desalted krill lipids described above, the methods are generally applicable any lipid fractions that contain phospholipids.

Accordingly, in some embodiments, the dry matter content of a lipid composition containing phospholipids is adjusted to a predetermined level by adding or removing solvent and the resulting is allowed to fractionate so that the phospholipids are predominantly partitioned into one phase and the neutral lipids partitioned into a different phase. In some embodiments, a lipid composition containing phospholipids such as the desalted krill lipids is mixed with a suitable protic solvent, preferably ethanol, so that the dry matter (i.e., lipid) content of the resulting solution is from about 10% to 40% w/w, preferably about 15% to 35% w/w, more preferably about 18% to 30% w/w, and most preferably about 20% to 25% w/w. In embodiments where the desalting step already provides the lipids in a suitable protic alcohol solution, such as is the case where ethanol is used as the solvent for chromatography, the desalted krill lipid solution may preferably be evaporated to provide desired dry matter content, i.e., from about 10% to 40% w/w, preferably about 15% to 35% w/w, more preferably about 18% to 28% w/w, and most preferably about 20% to 22% w/w. Suitable methods for evaporation include, but are not limited to, evaporation under reduced pressure (e.g., vacuum distillation), falling film evaporation, and removal of solvents via a membrane.

Following adjustment of the dry matter content to the desired level by either adding or removing solvent, the solution is then allowed to fractionate into an upper, light phase solution with an enhanced phospholipid content and a lower, heavy phase solution containing predominantly neutral lipids and a high level of astaxanthin. Preferably, the temperature of the solution during the fractionation step is controlled. In some embodiments, the temperature for the fractionation step is from about 0° C. to about 20° C., preferably from about 5° C. to about 15° C., more preferably from about 8° C. to about 12° C., and most preferably about 10° C.

In some embodiments, the concentration of the protic solvent may be varied in order to control the phospholipid concentration in the lipid composition of the upper phase. In some embodiments, the protic solvent has a concentration of from about 55% to 100%, more preferably about 65% to 98%. In some preferred embodiments, the protic solvent has a concentration of from about 90% to 100%, more preferably about 92% to 98%, and most preferably about 95%. In these embodiments, the phospholipid content on a dry matter basis of the lipids in the upper phase after fractionation is from about 50% to 70% w/w, preferably about 55% to 65% w/w and most preferably about 60% w/w. In still other preferred embodiments, the protic solvent has a concentration of from about 80% to 90% w/w, more preferably about 82% to 88% w/w, and most preferably about 85% w/w. In these embodiments, the phospholipid content on a dry matter basis of the lipids in the upper phase after fractionation is from about 70% to 90% w/w, preferably about 75% to 85% w/w and most preferably about 80% w/w.

In some embodiments, the upper and lower phases are separated by centrifugation, preferably cryocentrifugation with a two phase or three phase separator. In some embodiments, the centrifugation is conducted at from about 0° C. to about 30° C., more preferably from about 0° C. to about 10° C. and most preferably from about 3° C. to about 7° C. In general, the gravitational force utilized will depend on delta T between the phases. Lower temperatures provide a greater delta T. In some preferred embodiments, the G force employed in the separation is from about 8000×G to about 15000×G.

In some embodiments, the process steps of adjusting the dry matter content as described above through the centrifugation steps are repeated one or more times.

In some embodiments, the upper light phase is collected and processed further. The solvent is preferably removed from the upper phase by one or more evaporation steps to yield a krill phospholipid concentrate. The krill phospholipid concentrates preferably comprise from about 50% to 85% w/w phospholipids, and more preferably from about 55% to 80% w/w phospholipids, wherein w/w refers to the weight of phospholipids as a percent of the total weight of the concentrate.

In some embodiments, the lower heavy phase is collected and processed further. In some embodiments, the solvent is removed from the lower phase to provide a krill neutral lipid concentrate. In some embodiments, the lower phase may be fractionated with protic solvent and subjected to a second centrifugation step to recover additional phospholipids not recovered in the first fractionation step. Again, the solvent is removed from the resulting lower phase to provide a krill neutral lipid concentrate. The krill neutral lipid concentrate in both instances in characterized in containing high levels of astaxanthin. In some embodiments, the krill neutral lipid concentrate may be combined or blended with the krill phospholipid concentrate to provide a lipid composition with desired levels of phospholipids, neutral lipids, and astaxanthin. In some embodiments, the krill neutral lipid concentrate may be further processed (e.g., by chromatography) to provide an astaxanthin concentrate. The astaxanthin concentrate may then be combined or blended with the krill phospholipid concentrate to provide a lipid composition with desired levels of phospholipids and astaxanthin.

In some embodiments, the processes further comprises the step of adding a triglyceride oil, such as medium chain triglyceride oil or long chain triglyceride oil, at any stage during the process. For example, the triglyceride oil may be added to the collected light phase, heavy phase, phospholipid concentrate or neutral lipid concentrate. In some embodiments, the process steps of adjusting the dry matter content as described above through the centrifugation steps and/or evaporation steps are repeated one or more times.

In some embodiments, krill phospholipid and neutral lipid concentrates are produced by a further chromatography step. In these embodiments, at least a portion of the desalted lipid rich stream described above is introduced into to a polar liquid extraction zone comprising a fixed bed adsorber containing a macroporous styrenic polymeric bead type resin effective to adsorb neutral lipids. In preferred embodiments, the fixed bed chromatography step provides a polar lipid extract stream comprising solvent and at least 50 wt-% polar lipids on a dry basis. In some preferred embodiments, the fixed bed adsorber is intermittently regenerated with a hot ethanol stream at a hot regeneration temperature between about 40° C. and about 60° C. to provide a neutral lipid raffinate stream comprising solvent, neutral lipids and astaxanthin. In some embodiments, solvent is recovered polar lipid extract stream to provide a krill phospholipid concentrate and from the neutral lipid raffinate stream to provide a neutral lipid concentrate. These processes are described in more detail in co-pending U.S. application Ser. No. 14/619,102, which is incorporated herein by reference in its entirety.

In some embodiments, the krill phospholipid concentrates on a dry matter basis preferably comprise from about 5% w/w to 35% w/w triglycerides, more preferably from about 10% w/w to about 30% w/w triglycerides, and most preferably about 15% to 25% w/w triglycerides, wherein w/w refers to the weight of the triglycerides as a percent of the total krill phospholipid concentrate weight. In some embodiments, the krill phospholipid concentrates preferably comprise from about 2% w/w to 13% w/w free fatty acids, more preferably from about 4% w/w to about 11% w/w free fatty acids, and most preferably about 4% to 10% w/w free fatty acids, wherein w/w refers to the weight of the free fatty acids as a percent of the total krill phospholipid concentrate weight. In some embodiments, the krill phospholipid concentrates preferably comprise from about 0.5% w/w to 10% w/w lysophospholipids, more preferably from about 0.8% w/w to about 7.0% w/w lysophospholipids, and most preferably less than about 5.0% w/w or 3.0% w/w lysophospholipids, wherein w/w refers to the weight of the lysophospholipids as a percent of the total krill phospholipid concentrate weight. In some embodiments, the krill phospholipid concentrates preferably comprise less than about 1% w/w inorganic salts, more preferably less than about 0.5% w/w inorganic salts, even more preferably less than about 0.2% w/w inorganic salts, and most preferably less than about 0.1% or 0.05% w/w inorganic salts, wherein w/w refers to the weight of the inorganic salts as a percent of the total krill phospholipid concentrate weight. In some embodiments, the krill phospholipid concentrate preferably comprises less than about 5 mg N/100 g, more preferably less than about 3 mg N/100 g, even more preferably less than about 2 mg N/100 g, and most preferably less than about 1 mg N/100 g, where the N content serves as a convenient proxy for trimethylamine oxide (TMAO) content. In some embodiments, the krill phospholipid concentrates comprise less than about 10 ppm copper ($Cu^{++}$), more preferably less than about 5 ppm $Cu^{++}$, even more preferably less than about 2 ppm $Cu^{++}$, and most preferably less than about 1 ppm $Cu^{++}$. In some embodiments, the krill phospholipid concentrates comprise less than about 10 ppm total arsenic ($As^{3+}$), more preferably less than about 5 ppm total arsenic, even more preferably less than about 3 ppm total arsenic, and most preferably less than about 1 ppm total arsenic. In some embodiments, the krill phospholipid concentrate preferably comprise from about 0.01% to 2% w/w ethyl esters, more preferably from about 0.01% to about 1.5% w/w ethyl esters, and most preferably from about 0.01% to about 1% w/w ethyl esters, wherein w/w refers to the weight of the ethyl esters as a percent of the total krill phospholipid concentrate weight. In some embodiments, the krill phospholipid concentrate preferably comprise less than about 5%, 4%, 3% or 2% w/w ethyl esters down to a lower limit of 0.01% ethyl esters (i.e., between 5% and 0.01% w/w ethyl esters, between 4% and 0.01% w/w ethyl esters, between 3% and 0.01% w/w ethyl esters, or between 2% and 0.01% w/w ethyl esters), more preferably less than about 1.5% w/w ethyl esters, and most preferably less than about 1% w/w ethyl esters, wherein w/w refers to the weight of the ethyl esters as a percent of the total krill phospholipid concentrate weight. In some embodiments, the krill phospholipid concentrate have a conductivity of less than about 50 μS/cm when measured with 5% dry matter in 95% ethanol, more preferably a conductivity of less than about 30 μS/cm when measured with 5% dry matter in 95% ethanol, and most preferably a conductivity of less than about 20 μS/cm, 10 μS/cm, 5 μS/cm or 1 μS/cm when measured with 5% dry matter in 95% ethanol. In some embodiments, the krill phospholipid concentrate has a viscosity of from about 400 to 2000 mPas at 35° C., more preferably from about 500 to 1800 mPas at 35° C., and most preferably from about 600 to 1600 mPas at 35° C. In some embodiments, the krill phospholipid concentrate has a pH of from about 6.7 to 8.3 when measured in 95% ethanol.

In some embodiments, the krill neutral lipid concentrates preferably comprise on a dry matter basis from about 70% w/w to 95% w/w triglycerides, more preferably from about 75% w/w to about 95% w/w triglycerides, and most preferably about 88% to 92% w/w triglycerides, wherein w/w refers to the weight of the triglycerides as a percent of the total krill neutral lipid concentrate weight. In some embodiments, the krill neutral lipid concentrates preferably comprise from about 2% w/w to 20% w/w phospholipids, more preferably from about 4% w/w to about 15% w/w phospholipids, and most preferably about 5% to 10% w/w phospholipids, wherein w/w refers to the weight of the phospholipids as a percent of the total krill neutral lipid concentrate weight.

In some embodiments, the krill neutral lipid concentrates preferably comprise from about 0.5% w/w to 10% w/w free fatty acids, more preferably from about 1% w/w to about 8% w/w free fatty acids, and most preferably about 1% to 5% w/w free fatty acids, wherein w/w refers to the weight of the free fatty acids as a percent of the total krill neutral lipid concentrate weight. In some embodiments, the krill neutral lipid concentrates preferably comprise from about 0.1% w/w to 2% w/w lysophospholipids, more preferably from about 0.2% w/w to about 1.0% w/w lysophospholipids, and most preferably less than about 0.5% w/w or 0.2% w/w lysophospholipids, wherein w/w refers to the weight of the lysophospholipids as a percent of the total krill neutral lipid concentrate weight. In some embodiments, the krill neutral lipid concentrates preferably comprise less than about 1% w/w inorganic salts, more preferably less than about 0.5% w/w inorganic salts, even more preferably less than about 0.2% w/w inorganic salts, and most preferably less than about 0.1% or 0.05% w/w inorganic salts, wherein w/w refers to the weight of the inorganic salts as a percent of the total krill neutral lipid concentrate weight. In some embodiments, the krill neutral lipid concentrate preferably comprises less than about 5 mg N/100 g, more preferably less than about 3 mg N/100 g, even more preferably less than about 2 mg N/100 g, and most preferably less than about 1 mg N/100 g, where the N content serves as a convenient proxy for trimethylamine oxide (TMAO) content. In some embodiments, the krill neutral lipid concentrates comprise less than about 10 ppm copper ($Cu^{++}$), more preferably less than about 5 ppm $Cu^{++}$, even more preferably less than about 2 ppm $Cu^{++}$, and most preferably less than about 1 ppm $Cu^{++}$. In some embodiments, the krill neutral lipid concentrates comprise less than about 10 ppm total arsenic ($As^{3+}$), more preferably less than about 5 ppm total arsenic, even more preferably less than about 3 ppm total arsenic, and most preferably less than about 1 total ppm arsenic. In some embodiments, the krill neutral lipid concentrate preferably comprise from about 0.01% to 2% w/w ethyl esters, more preferably from about 0.01% to about 1.5% w/w ethyl esters, and most preferably from about 0.01% to about 1% w/w ethyl esters, wherein w/w refers to the weight of the ethyl esters as a percent of the total krill neutral lipid concentrate weight. In some embodiments, the krill neutral lipid concentrate preferably comprise less than about 2% w/w ethyl esters, more preferably less than about 1.5% w/w ethyl esters, and most preferably less than about 1% w/w ethyl esters, wherein w/w refers to the weight of the ethyl esters as a percent of the total krill neutral lipid concentrate weight. In some embodiments, the krill neutral lipid concentrate have a conductivity of less than about 50 μS/cm when measured with 5% dry matter in 95% ethanol, more preferably a conductivity of less than about 30 μS/cm when measured with 5% dry matter in 95% ethanol, and most preferably a conductivity of less than about 20 μS/cm, 10 μS/cm, 5 μS/cm or 1 μS/cm when measured with 5% dry matter in 95% ethanol. In some embodiments, the krill neutral lipid concentrate has a viscosity of less than about 400 mPas at 25° C., more preferably less than about 300 mPas at 25° C., and most preferably less than about 200 mPas at 25° C. In some embodiments, the krill neutral lipid concentrate has a pH of from about 7.0 to 9.0 when measured in 95% ethanol.

In some embodiments, the neutral lipid concentrate may be preferably further processed to provide an astaxanthin ester concentrate. In some embodiments, the astaxanthin ester concentrate is produced by introducing all or at least a portion of the neutral lipid raffinate stream to an astaxanthin extraction zone and therein contacting a steam activated carbon adsorbent to adsorb astaxanthin and provide a neutral lipid rich stream comprising solvent and neutral lipids, and regenerating the steam activated carbon with anisole to desorb the astaxanthin to provide an astaxanthin rich stream comprising anisole and astaxanthin. In some embodiments, the anisole is preferably recovered from the astaxanthin rich stream to provide an astaxanthin ester concentrate. These processes are described in more detail in co-pending U.S. application Ser. No. 14/619,102, which is incorporated herein by reference in its entirety. In some preferred embodiments, the astaxanthin ester concentrate comprises from about 300 or 400 ppm to about 4000 ppm astaxanthin esters, more preferably from about 400 to about 3000 ppm astaxanthin esters and most preferably greater than about 500 ppm astaxanthin esters. In further preferred embodiments, the astaxanthin ester concentrates comprise greater than about 95%, 96%, 97%, 98% or 99% w/w krill neutral lipids, wherein wherein w/w refers to the weight of the neutral krill lipids as a percent of the total astaxanthin ester concentrate weight.

5. Formulation of Krill Phospholipid Compositions

The krill phospholipid compositions of the present invention are preferably administered orally. Accordingly, in some embodiments, the compositions of this invention (such as those described in the preceding sections) are contained in acceptable excipients and/or carriers for oral consumption. The actual form of the carrier, and thus, the composition itself, is not critical. The carrier may be a liquid, gel, gelcap, capsule, powder, solid tablet (coated or non-coated), tea, or the like. The composition is preferably in the form of a tablet or capsule and most preferably in the form of a soft gel capsule. Suitable excipient and/or carriers include vegetable oil, fish oil, krill oil, maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of Remington's Pharmaceutical Sciences (Maack Publishing Co., Easton, Pa.). For intravenous or oral administration, the omega-3 compounds and compositions of the present invention may preferably be provided as emulsions.

In some embodiments, the krill phospholipid compositions are formulated for oral administration with flavoring agents or sweeteners. Examples of useful flavoring include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee. In one embodiment, the dietary supplement contains cocoa or chocolate. Emulsifiers may be added for stability of the final product. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product. In addition to the carbohydrates described above, the nutritional supplement can contain natural or artificial (preferably low calorie) sweeteners, e.g., saccharides, cyclamates, aspartamine, aspartame, acesulfame K, and/or sorbitol.

The krill phospholipid compositions of the present invention may also be delivered as dietary supplements, nutritional supplements, or functional foods.

The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like. For example, the dietary supplement of the present invention may contain one or more of the following: asorbates (ascorbic acid, mineral ascorbate salts, rose hips, acerola, and the like), dehydroepiandosterone (DHEA), green tea (polyphenols), inositol, kelp, dulse, bioflavinoids, maltodextrin, nettles, niacin, niacinamide, rosemary, selenium, silica (silicon dioxide, silica gel, horsetail, shavegrass, and the like), spirulina, zinc, and the like. Such optional ingredients may be either naturally occurring or concentrated forms.

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

In other embodiments, the present invention provides nutritional supplements (e.g., energy bars or meal replacement bars or beverages) comprising of the krill phospholipid compositions of the present invention. In preferred embodiments, the nutritional supplements comprise an effective amount of the components as described above. The nutritional supplement may serve as meal or snack replacement and generally provide nutrient calories. Preferably, the nutritional supplements provide carbohydrates, proteins, and fats in balanced amounts. The nutritional supplement can further comprise carbohydrate, simple, medium chain length, or polysaccharides, or a combination thereof. A simple sugar can be chosen for desirable organoleptic properties. Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are mono- or disaccharides. The nutritional supplement contains, in one embodiment, combinations of sources of carbohydrate of three levels of chain length (simple, medium and complex; e.g., sucrose, maltodextrins, and uncooked cornstarch).

In still further embodiments, the present invention provides food products, prepared food products, or foodstuffs (i.e., functional foods) comprising the krill phospholipid compositions of the present invention. In preferred embodiments, the foods comprise an effective amount of the components as described above. For example, in some embodiments, beverages and solid or semi-solid foods comprising the fatty acids or derivatives thereof are provided. These forms can include, but are not limited to, beverages (e.g., soft drinks, milk and other dairy drinks, and diet drinks), baked goods, puddings, dairy products, confections, snack foods, or frozen confections or novelties (e.g., ice cream, milk shakes), prepared frozen meals, candy, snack products (e.g., chips), soups, spreads, sauces, salad dressings, prepared meat products, cheese, yogurt and any other fat or oil containing foods, and food ingredients (e.g., wheat flour).

In some preferred embodiments, the krill phospholipid compositions are incorporated into chewable matrices. Preferred chewable matrices jelly candies and gelatin-based gummi candy. Exemplary gummi candies include gummi bears, gummi worms, gummi frogs, gummi hamburgers, gummi cherries, gummi soda bottles, gummi sharks, gummi army men, gummi hippopotami, gummi lobsters, gummi watermelons, gummi octopuses, gummi apples, gummi peaches, and gummi oranges. The terms "gummi" and "gummy" are used interchangeably herein.

In some particularly preferred embodiments, the chewable matrix material is a sweetened material commonly referred to a gummy candy or jelly material. Gummy candy or jelly sweets are a broad general type of gelatin based, chewy candy. Gummy bears are the most popular and well known of the gummy candies. Other shapes are provided as well and gummy candies are sometimes combined with other forms of candy such as marshmallows and chocolates and as well made sour.

In preferred embodiments, the chewable matrix material comprises a gelling agent, which may be any physiologically tolerable gelling agent (preferably a saccharide (e.g. an oligosaccharide or polysaccharide), a protein or a glycoprotein) or combination capable of forming a soft, chewable, self-supporting chewable gel. Many such materials are known from the food and pharmaceutical industry and are discussed for example in Handbook of hydrocolloids, G O Phillips and P A Williams (Eds.), Woodhead Publishing, Cambridge, UK, 2000. The gelling agents are preferably materials capable of undergoing a sol-gel transformation, e.g. under the influence of a change in physiochemical parameters such as temperature, pH, presence of metal ions (e.g. group 1 or 2 metal ions), etc. Preferred gelling agents include gelatins, alginates and carageenans. However, the use of gelatins is especially preferred as breakdown in the throat of trapped fragments is ensured and as cores having the desired properties may readily be produced using gelatins.

The gelatins used as gelling agents in the chewable matrix of the invention may be produced from the collagen of any mammal or the collagen of any aquatic species, however the use of gelatin from salt-water fish and in particular cold and warm water fishes is preferred. Gelatins having an amino acid content of 5 to 25% wt. are preferred, more especially those having an amino acid content of 10 to 25% wt. The gelatins will typically have a weight average molecular weight in the range 10 to 250 kDa, preferably 75 to 220 kDa, especially 80 to 200 kDa. Gelatins having no Bloom value or low Bloom values of 60-300, 150-300 and especially 90-200 are preferred. Where a gelatin of no Bloom value, e.g. a cold water fish gelatin, is used, this will typically be used together with another gelatin or other gelling agent. The combination of cold water and warm water fish gelatins is especially preferred. The gelatin will typically be present in the aqueous phase at a concentration of 1 to 50% wt., preferably 2 to 35% wt., particularly 5 to 25% wt. In the case of mixtures of gelatin and polysaccharides, the weight ratio of gelatin to polysaccharide in the aqueous phase will typically be 50:1 to 5:1, preferably 40:1 to 9:1, especially 20:1 to 10:1.

Where polysaccharides, or mixtures of polysaccharides and gelatin are used as the gelling agent, it is preferred to use natural polysaccharides, synthetic polysaccharides or semi-synthetic polysaccharides, e.g. polysaccharides from plants, fish, terrestrial mammals, algae, bacteria and derivatives and fragmentation products thereof. Typical marine polysaccharides include carageenans, alginates, agars and chitosans.

Typical plant polysaccharides include pectins. Typical microorganism polysaccharides include gellans and scleroglucans. The use of charged, e.g. electrostatically charged and/or sulphated polysaccharides is preferred, as is the use of marine polysaccharides, in particular carageenans, and alginates, especially carageenans. The carageenan family, which includes iota- and kappa-carageenans, is a family of linear sulphated polysaccharides produced from red algae. The repeating disaccharide unit in kappa-carrageenan is β-D-galactose-4-sulphate and 3,6-anhydro-α-D-galactose, while that in iota-carrageenan is β-D-galactose-4-sulphate and 3,6-anhydro-α-D-galactose-2-sulphate. Both kappa- and iota-carageenans are used in food preparations. The carageenans are used as stabilisers, emulsifiers, gelling agents and fat replacers.

Both iota and kappa carageenans form salt- or cold-setting reversible gels in an aqueous environment. Coil-helix transition and aggregation of helices form the gel network. Kappa-carrageenan has binding sites for specific monovalent cations, resulting in gel formation with decreasing shear and elastic moduli in the order $Cs^+>K^+>>Na^+>Li^+$. As a rule, an increasing salt concentration enhances the elastic modulus and the setting and melting temperatures of a kappa-carrageenan gel. The use of water-soluble potassium, rubidium, or caesium compounds, particularly potassium compounds, and particularly naturally occurring compounds (e.g. salts) is preferred when kappa-carrageenan is used according to the invention, e.g. at concentrations of up to 100 mM, more especially up to 50 mM. A salt-dependent conformational transition is also found for iota-carrageenan. The molecules are also known to undergo coil-helix transition with strong helix-stabilisation in the presence of multivalent cations, like $Ca^{2+}$. The use of water-soluble calcium, strontium, barium, iron or aluminium compounds, especially calcium compounds, and particularly naturally occurring compounds (e.g. salts) is preferred when iota-carrageenan is used according to the invention, e.g. at concentrations of up to 100% mM.

The polysaccharide gelling agents used according to the invention will typically have weight average molecular weights of 5 kDa to 2 MDa, preferably 10 kDa to 1 MDa, most preferably 100% kDa to 900 kDa, particularly 200 to 800 kDa. They will typically be used at concentrations of 0.01 to 5% wt, preferably 0.1 to 1.5% wt., particularly 0.2% to 1% wt in the aqueous phase. Where mono or multivalent cations, typically group 1 or group 2 metal ions, are included in the aqueous phase, this will typically be at concentrations in the range 2.5 to 100% mM, particularly 5 to 50 mM.

Besides the gelling agent and water and any required gelling initiator, other physiologically tolerable materials may be present in the chewable matrix, e.g. emulsifiers, emulsion stabilizers, pH modifiers, viscosity modifiers, sweeteners, fillers, vitamins (e.g. vitamin C, thiamine, riboflavin, niacin, vitamin B6, vitamin B12, folacin, panthotenic acid), minerals, aromas, flavors, making agents, colors, physiologically active agents, etc., as described above in detail in relation to addition materials that can be included in the oxidizable fatty acid composition.

The chewable matrix preferably has a gelling temperature in the range 10 to 30 C, more preferably 15 to 28 C, and a melting temperature in the range 20 to 80 C, more preferably 24 to 60 C, especially 28 to 50 C.

Where a sweetener is included in the chewable matrix, this will typically be selected from natural sweeteners such as sucrose, fructose, glucose, reduced glucose, maltose, xylitol, maltitol, sorbitol, mannitol, lactitol, isomalt, erythritol, polyglycitol, polyglucitol, glycerol, stevia, agave nectar, inverti syrup and artificial sweeteners such as aspartame, acesulfame-K, neotame, saccharine, sucralose. The use of non-cariogenic sweeteners is preferred and the use of xylitol is especially preferred. Preferred flavorings include orange, raspberry, cherry, lemon, blood orange, grapefruit, strawberry, blueberry, blackberry and combinations thereof, especially orange and raspberry.

Mass production of gummi confection (e.g., gummi bears) includes mixing the gummi confection ingredients and pouring the resulting mixture into many starched-lined (e.g., corn starch-lined) trays/molds. The corn starch prevents the gummy bears from sticking to the mold and lets them release easily once they are set. First, the desired character molds are created and, if necessary, duplicated with a machine. Optionally, starch powder is applied to the character molds. Gummi confection ingredients, such as sugar, glucose syrup, gelatin, and water are mixed together and heated. In one aspect, the ingredients are mixed with colors and flavors that give the bears their signature look and taste. The molten gelatin mixture is poured into the molds and allowed to cool and set prior to packaging or consumption. Preferably, the gummi confection is subsequently heated and placed in a large drum tumbler to apply a composition of isolated Bacillus coagulans and a sweetener (e.g., a sugar).

In some preferred embodiments, production of gummi confection includes the following. A colloid batch and a puree batch are formed and combined with corn syrup and sugar to form a base slurry. The colloid batch comprises a solution of the gelling agent in water at a level of from 5 to 15% by weight of the gelling agent, more preferably from 7 to 12% of the gelling agent based on the total weight of the colloid batch. The colloid batch is held at a temperature of 170 to 190 F. The puree batch preferably comprises water, fruit puree and/or high fructose corn syrup or other sweeteners, thin boiling starch, and sodium citrate. It is held at a temperature of from 65 to 75 F. Preferably, the fruit puree has a Brix of from 10 to 45, more preferably from 25 to 40. Optionally, the puree batch includes a plurality of fruit purees. The fruit puree comprises a typical fruit puree, a fruit juice, or a fruit powder. The puree batch comprises from 30 to 40% by weight water, from 0 to 40% by weight fruit puree, from 0 to 40% by weight high fructose corn syrup, from 25 to 35% by weight thin boiling starch, and from 0.0 to 2.0% by weight sodium citrate. In a mixing kettle from 25 to 40% by weight of additional corn syrup is combined with from 15 to 40% by weight of fine granulated sugar, from 10 to 15% by weight of the colloid batch and from 20 to 30% by weight of the puree batch to form the base slurry. Preferably, the corn syrup is approximately 42 DE corn syrup, however, as would be understood by one of ordinary skill in the art other DE corn syrups could be used. The base slurry components are completely mixed and held at 130 to 150 F in a holding tank.

The base slurry is then cooked to bring the Brix to from 70 to 85 Brix, more preferably to a Brix of from 75 to 80. In one embodiment the base slurry is passed through a coil cooker and heated to a temperature of from 250 to 325 F to cook it. Other cooking methods could be used as will be understood by one of ordinary skill in the art. The cooked base slurry is preferably subjected to vacuum to further increase the Brix into the desired range. The cooked base slurry is held at approximately 200 F until used. An acidulant solution is preferably added along with color and flavor to the cooked base slurry just prior to deposition in the starch molds. In one aspect, the acidulant solution comprises ascorbic acid present in an amount of from 15 to 20% by weight, citric acid present in an amount of from 10 to 20% by weight, and malic acid present in an amount of from 5 to 10% by weight with the remainder comprising water. As would be understood by one of ordinary skill in the art, other edible acids could be used in place of or in addition to those listed. In one aspect, 95 to 97% by weight of cooked base slurry is combined with from 2 to 3% by weight of the acidulant solution and the remainder comprises flavors and colors. Optionally, the acidulant solution is used to bring the pH of the base slurry to from 2.6 to 3.2. One of ordinary skill in the art would have no difficulty selecting suitable colors and flavors. The combined mixture is then deposited into starch molds, e.g., using a Mogul starch molding machine. Such starch molding machines are well known by those of ordinary skill in the art. In one aspect, from 0.3 to 3 grams of the base slurry is deposited into each mold cavity. In some preferred embodiments, the starch molding machine ("Mogul") used to form the gummy bears comprises two nozzles for each mold, and a device for delivery of small softgel capsules. The first nozzle provides about 40% of the volume of the mold before one capsule is placed in the mold. Finally, the second nozzle fills up the mold. The gummy bear containing the capsule is then quickly cooled. The starch trays with deposited base slurry are transferred to a drying room where there are held for 12 to 48 hours. Optionally, the trays are first held at a temperature of from 130 to 150 F for from 10 to 15 hours, and then cooled to 70 to 80 F and held at that temperature for from 6 to 12 hours. The gelled starch molded food pieces are then removed from the trays, the starch is recycled.

In some embodiments of the invention, it is contemplated that oil inside the capsule is protected from hydrolysis by water present in the product. Gummy candies and other jelly sweets contain rather high amounts of water and further, the acidity is low to counteract growth of bacteria.

In some embodiments, the present invention provides compositions comprising the krill phospholipid compositions described above and one or more additional omega-3 fatty acid derivatives or free fatty acids. The omega-3 fatty acid derivatives or free fatty acids may be derived from the neutral lipid extract or from an additional source, such as fish oil or omega-3 ester concentrate. In some embodiments, the one or more additional omega-3 fatty acid derivatives are selected from omega-3 esters and glycerides. For example, in some embodiments, the composition may comprise from about 1% to about 60% w/w of the krill oil composition (i.e., weight of phospholipid compounds/total weight of composition), with the remaining 99% to 40% w/w of the composition being omega-3 glycerides, esters, or free fatty acids or a combination thereof (i.e., weight of omega-3 glycerides, esters, or free fatty acids or a combination thereof/total weight of the composition). In some embodiments, the composition may comprise from about 5% to about 60% w/w phospholipids, with the remaining 95% to 40% w/w of the composition being omega-3 glycerides, esters, or free fatty acids or a combination thereof. In some embodiments, the composition may comprise from about 20% to about 60% w/w phospholipids, with the remaining 80% to 40% w/w of the composition being omega-3 glycerides, esters, or free fatty acids or a combination thereof. In some embodiments, the composition may comprise from about 30% to about 60% w/w phospholipids, with the remaining 70% to 40% w/w of the composition being omega-3 glycerides, esters, or free fatty acids or a combination thereof. In some embodiments, the composition may comprise from about 40% to about 60% w/w phospholipids, with the remaining 60% to 40% w/w of the composition being omega-3 glycerides, esters, or free fatty acids or a combination thereof. In some embodiments, the composition may comprise from about 50% to about 60% w/w phospholipids, with the remaining 50% to 40% w/w of the composition being omega-3 glycerides, esters, or free fatty acids or a combination thereof.

6. Uses of Krill Phospholipid Compositions

In some embodiments, the compounds or compositions described above are administered to a subject in need thereof to treat a disease or condition associated with red blood cells and cell membranes, and in particular a disease or conditions associated with an abnormality in red blood cells of cell membranes. In some embodiments, the condition or disease is sickle cell disease, sickle cell anemia, or sickle cell trait. In some embodiments, the condition or disease is thalassemia (alpha-, beta- or delta-), thalassemia in combination with a hemoglobinopathy (Hemoglobin E, Hemoglobin S, or Hemoglobin C), splenomegaly, or membrane abnormities such as acanthocytes or spur/spike cells, codocytes (target cells), echinocytes (burr cells), elliptocytes and ovalocytes, spherocytes, stomatocytes (mouth cells) and degmacytes ("bite cells").

In some embodiments, an effective amount of the compounds or compositions described above are administered to a subject in need thereof to treat or prevent a cardiovascular disorder or metabolic syndrome. In some embodiments, the cardiovascular disorder is selected from atherosclerosis, arteriosclerosis, coronary heart (carotid artery) disease (CHD or CAD), acute coronary syndrome (or ACS), valvular heart disease, aortic and mitral valve disorders, arrhythmia/atrial fibrillation, cardiomyopathy and heart failure, angina pectoris, acute myocardial infarction (or AMI), hypertension, orthostatic hypotension, shock, embolism (pulmonary and venous), endocarditis, diseases of arteries, the aorta and its branches, disorders of the peripheral vascular system (peripheral arterial disease or PAD), Kawasaki disease, congenital heart disease (cardiovascular defects) and stroke (cerebrovascular disease), dyslipidemia, hypertriglyceridemia, hypertension, heart failure, cardiac arrhythmias, low HDL levels, high LDL levels, stable angina, coronary heart disease, acute myocardial infarction, secondary prevention of myocardial infarction, cardiomyopathy, endocarditis, type 2 diabetes, insulin resistance, impaired glucose tolerance, hypercholesterolemia, stroke, hyperlipidemia, hyperlipoproteinemia, chronic kidney disease, intermittent claudication, hyperphosphatemia, omega-3 deficiency, phospholipid deficiency, carotid atherosclerosis, peripheral arterial disease, diabetic nephropathy, hypercholesterolemia in HIV infection, acute coronary syndrome (ACS), non-alcoholic fatty liver disease/non-alcoholic steatohepatitis (NAFLD/NASH), arterial occlusive diseases, cerebral atherosclerosis, arteriosclerosis, cerebrovascular disorders, myocardial ischemia, coagulopathies leading to thrombus formation in a vessel and diabetic autonomic neuropathy.

In some embodiments, an effective amount of the compounds or compositions described above are administered to a subject in need thereof to treat, prevent, or improve cognition and/or a cognitive disease, disorder or impairment (memory, concentration, learning (deficit)), or to treat or prevent neurodegenerative disorders. In some embodiments, the cognitive disease, disorder or impairment is selected from Attention Deficit Disorder (ADD), Attention Deficit Hyperactivity Disorder (ADHD), autism/autism spectrum disorder (ASD), (dyslexia, age-associated memory impairment and learning disorders, amnesia, mild cognitive impairment, cognitively impaired non-demented, pre-Alzheimer's disease, Alzheimer's disease, epilepsy, Pick's disease, Huntington's disease, Parkinson disease, Lou Gehrig's disease, pre-dementia syndrome, Lewy body dementia dementia, dentatorubropallidoluysian atrophy, Freidreich's ataxia, multiple system atrophy, types 1, 2, 3, 6, 7 spinocerebellar ataxia, amyotrophic lateral sclerosis, familial spastic paraparesis, spinal muscular atrophy, spinal and bulbar muscular atrophy, age-related cognitive decline, cognitive deterioration, moderate mental impairment, mental deterioration as a result of ageing, conditions that influence the intensity of brain waves and/or brain glucose utilization, stress, anxiety, concentration and attention impairment, mood deterioration, general cognitive and mental well being, neurodevelopmental, neurodegenerative disorders, hormonal disorders, neurological imbalance or any combinations thereof. In a specific embodiment, the cognitive disorder is memory impairment.

In some embodiments, an effective amount of the compounds or compositions described above are administered to a subject in need thereof to inhibit, prevent, or treat inflammation or an inflammatory disease. In some embodiments, the inflammation or inflammatory disease is selected from organ transplant rejection; reoxygenation injury resulting from organ transplantation (see Grupp et al., J. Mol. Cell. Cardiol. 31: 297-303 (1999)) including, but not limited to, transplantation of the following organs: heart, lung, liver and kidney; chronic inflammatory diseases of the joints, including arthritis, rheumatoid arthritis, osteoarthritis and bone diseases associated with increased bone resorption; inflammatory bowel diseases (IBD) such as ileitis, ulcerative colitis (UC), Barrett's syndrome, and Crohn's disease (CD); inflammatory lung diseases such as asthma, acute respiratory distress syndrome (ARDS), and chronic obstructive pulmonary disease (COPD); inflammatory diseases of the eye including corneal dystrophy, trachoma, onchocerciasis, uveitis, sympathetic ophthalmitis and endophthalmitis; chronic inflammatory diseases of the gum, including gingivitis and periodontitis; inflammatory diseases of the kidney including uremic complications, glomerulonephritis and nephrosis; inflammatory diseases of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, Epilepsy, amyotrophic lateral sclerosis and viral or autoimmune encephalitis, preeclampsia; chronic liver failure, brain and spinal cord trauma, and cancer. The inflammatory disease can also be a systemic inflammation of the body, exemplified by gram-positive or gram negative shock, hemorrhagic or anaphylactic shock, or shock induced by cancer chemotherapy in response to proinflammatory cytokines, e.g., shock associated with proinflammatory cytokines. Such shock can be induced, e.g., by a chemotherapeutic agent that is administered as a treatment for cancer. Other disorders include depression, obesity, allergic diseases, acute cardiovascular events, muscle wasting diseases, and cancer cachexia. Also inflammation that results from surgery and trauma can be treated with the phospholipid compositions.

In some embodiments, the effective amount comprises from about 0.1 to about 5 grams of the krill phospholipid composition, preferably from about 0.2% to about 3 grams of the krill phospholipid composition, and most preferably about 0.5 to about 1.5 grams of the krill phospholipid composition.

The krill phospholipid compositions of the present invention may be used to treat a variety of subjects. Suitable subjects include humans as well as domestic animals, non-human primates, and companion animals such as dogs, cats and birds.

EXAMPLES

Example 1

10.5 grams of a krill oil free of salts containing about 58% neutral lipids and 40.5% phospholipids (measured by P-NMR) was obtained. 1.75 grams of the krill oil was placed in each of six centrifuge tubes with 7.0 grams of 95% ethanol to provide a lipid solution with 20% dry matter. The tubes were shaken vigorously at room temperature and then centrifuged for 4 minutes at 4000 RPM, which provide 715×G at the top of the tube and 2000×G at the bottom of the tube. The tubes were then left over two nights at 10° C. The top light phase was removed and evaporated to dryness. The bottom heavy phase was also removed and evaporated to dryness.

The top phase volume at 20° C. was 92.5% of the initial solution. The dry matter yield at 10° C. was 6.27 grams or 60% of the initial dry matter. The phospholipid content of the dry matter was measured to be 60.8% by P-NMR. Approximately 90% of the phospholipids present in the original starting material was recovered in the upper phase. The astaxanthin ester content of the upper phase was measured to be approximately 52 ppm.

The bottom phase volume at 20° C. was 7.5% of the initial solution. The dry matter yield at 10° C. was 4.23 grams. The phospholipid content of the dry matter was calculated to be 9.65% by P-NMR, and the dry mater contained approximately 90% neutral lipids. The astaxanthin ester content of the bottom phase was calculated to be approximately 419 ppm.

Example 2

The example describes a process for making a crude krill lipid extract. 440 gram of 96% Ethanol containing 10 gram of 1M HCl was added to 100% gram of meal in a reactor and stirred for 45 minutes at 40 C. Then rector content was emptied through a filter to retain the meal/solid particles. The filtered extract was evaporated at 50 C under vacuum and 29.7 gram of dry matter was obtained (29.7% yield). The conductivity in the extract was measured to 616 uS/cm. This process yields a crude krill lipid extract which can subsequently be desalted and concentrated as described elsewhere herein.

Example 3

This example describes the use of alcohol fractionation and centrifugation to make a krill phospholipid concentrate. 10.23 gram of desalted oil with 35.60% PL was mixed with 41 gram of 95% ethanol and heavily shaken. The sample was then centrifuged at 6 C and 4000 rpm for 4 minutes. The upper phase was collected and evaporated to yield 6.16 gram of oil (61% yield). The oil contained 54.94% PL.

The invention claimed is:

1. A krill phospholipid composition comprising:
   from 50% to 85% w/w phospholipids;
   from 5% to 35% w/w triglycerides;
   and wherein the composition further has the following properties:
   the composition comprises from 2% w/w to 13% w/w free fatty acids;
   the composition comprises less than 1.0% w/w inorganic salts; and
   the composition comprises less than 10 ppm total arsenic.

2. The composition of claim 1, wherein the composition further has one or more of the properties:
   the composition comprises from 0.5% w/w to 10% w/w lysophospholipids;
   the composition comprises from 0.01% to 1% w/w ethyl esters;
   the composition is characterized in having a conductivity of less than 20 µS/cm when measured with 5% dry matter in 95% ethanol.

3. The composition of claim 1, wherein the composition further has two or more of the following properties:
   the composition comprises from 0.5% w/w to 10% w/w lysophospholipids;
   the composition comprises from 0.01% to 1% w/w ethyl esters; and
   the composition is characterized in having a conductivity of less than 20 µS/cm when measured with 5% dry matter in 95% ethanol.

4. The composition of claim 1, wherein the composition has the following properties:
   the composition comprises from 0.5% w/w to 10% w/w lysophospholipids;
   the composition comprises from 0.01% to 1% w/w ethyl esters; and
   the composition is characterized in having a conductivity of less than 20 µS/cm when measured with 5% dry matter in 95% ethanol.

5. The composition of claim 1, further comprising a second nutraceutical ingredient.

6. The composition of claim 1, further comprising a pharmaceutical carrier.

7. The composition of claim 1, wherein the composition is provided in a delivery vehicle selected from the group consisting of an oral delivery vehicle, a functional food, a nutritional supplement, a dietary supplement and a medical food.

8. The composition of claim 7, wherein said oral delivery vehicle is a soft gel capsule.

9. A krill phospholipid composition comprising:
   from 30% to 50% w/w phospholipids;
   from 32% to 52% w/w triglycerides;
   and wherein the composition further has the following properties:
   the composition comprises from 2% w/w to 13% w/w free fatty acids;
   the composition comprises less than 1.0% w/w inorganic salts; and
   the composition comprises less than 10 ppm total arsenic.

10. The composition of claim 9, wherein the composition further has one or more of the properties:

the composition comprises from 0.5% w/w to 10% w/w lysophospholipids;

the composition comprises from 0.01% to 1% w/w ethyl esters;

the composition is characterized in having a conductivity of less than 20 μS/cm when measured with 5% dry matter in 95% ethanol.

11. The composition of claim 9, wherein the composition further has two or more of the following properties:

the composition comprises from 0.5% w/w to 10% w/w lysophospholipids;

the composition comprises from 0.01% to 1% w/w ethyl esters; and the composition is characterized in having a conductivity of less than 20 μS/cm when measured with 5% dry matter in 95% ethanol.

12. The composition of claim 9, wherein the composition has the following properties:

the composition comprises from 0.5% w/w to 10% w/w lysophospholipids;

the composition comprises from 0.01% to 1% w/w ethyl esters; and the composition is characterized in having a conductivity of less than 20 μS/cm when measured with 5% dry matter in 95% ethanol.

13. The composition of claim 9, further comprising a second nutraceutical ingredient.

14. The composition of claim 9, further comprising a pharmaceutical carrier.

15. The composition of claim 9, wherein the composition is provided in a delivery vehicle selected from the group consisting of an oral delivery vehicle, a functional food, a nutritional supplement, a dietary supplement and a medical food.

16. The composition of claim 15, wherein said oral delivery vehicle is a soft gel capsule.

* * * * *